(12) United States Patent
Kudo et al.

(10) Patent No.: US 9,770,158 B2
(45) Date of Patent: Sep. 26, 2017

(54) HOLDING MECHANISM FOR ENDOSCOPE GUIDE MEMBER, AND ENDOSCOPE

(71) Applicant: OLYMPUS CORPORATION, Tokyo (JP)

(72) Inventors: Ryota Kudo, Sagamihara (JP); Naoya Ouchi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/137,173

(22) Filed: Apr. 25, 2016

(65) Prior Publication Data

US 2016/0235277 A1 Aug. 18, 2016

Related U.S. Application Data

(63) Continuation of application No. PCT/JP2015/059975, filed on Mar. 30, 2015.

(30) Foreign Application Priority Data

Apr. 23, 2014 (JP) ................................. 2014-089652

(51) Int. Cl.
*A61B 1/00* (2006.01)
*A61B 1/04* (2006.01)
*A61B 1/018* (2006.01)

(52) U.S. Cl.
CPC ........ *A61B 1/0014* (2013.01); *A61B 1/00087* (2013.01); *A61B 1/00137* (2013.01); *A61B 1/018* (2013.01)

(58) Field of Classification Search
CPC .. A61M 2025/09125; A61M 25/09041; A61M 2025/09116; A61M 25/09; A61B 1/018; A61B 1/00137

USPC ......................... 600/104, 114, 153–154, 159
See application file for complete search history.

(56) References Cited

U.S. PATENT DOCUMENTS

| 6,007,522 A | 12/1999 | Agro et al. |
|---|---|---|
| 2003/0073955 A1 | 4/2003 | Otawara |
| 2004/0162465 A1 | 8/2004 | Carrillo |
| 2005/0059890 A1 | 3/2005 | Deal et al. |
| 2005/0101836 A1 | 5/2005 | Onuki et al. |

(Continued)

FOREIGN PATENT DOCUMENTS

| CN | 103458762 A | 12/2013 |
|---|---|---|
| JP | S55-66340 A | 5/1980 |

(Continued)

OTHER PUBLICATIONS

International Search Report dated Jun. 23, 2015 issued in PCT/JP2015/059975.

(Continued)

*Primary Examiner* — Alexandra Newton
(74) *Attorney, Agent, or Firm* — Scully, Scott, Murphy & Presser, P.C.

(57) ABSTRACT

A holding mechanism includes a fixed holding portion and a rotary holding portion. The rotary holding portion switches the holding state of the holding mechanism by rotation to either a first state in which the rotary holding portion holds, together with the fixed holding portion, a guide member at the operation portion, or the second state in which the rotary holding portion fixes, together with the fixed holding portion, the guide member.

11 Claims, 18 Drawing Sheets

(56) References Cited

U.S. PATENT DOCUMENTS

| | | | |
|---|---|---|---|
| 2006/0195117 A1 | 8/2006 | Rucker et al. | |
| 2010/0145144 A1* | 6/2010 | Kitano | A61B 1/00098 600/107 |
| 2011/0071349 A1* | 3/2011 | Drontle | A61B 1/00165 600/106 |
| 2013/0217963 A1* | 8/2013 | Naito | A61B 1/0016 600/104 |

FOREIGN PATENT DOCUMENTS

| | | |
|---|---|---|
| JP | 64-54502 A | 4/1989 |
| JP | 2001-511023 A | 8/2001 |
| JP | 2001-340468 A | 12/2001 |
| JP | 2003-116777 A | 4/2003 |
| JP | 2007-500559 A | 1/2007 |
| JP | 2008-529723 A | 8/2008 |
| JP | WO 2013021710 A1 * 2/2013 ........... A61B 1/0016 |

OTHER PUBLICATIONS

English translation of International Preliminary Report on Patentability dated Nov. 3, 2016 together with the Written Opinion received in related International Application No. PCT/JP2015/059975.

Chinese Office Action dated Apr. 27, 2017 in Chinese Patent Application No. 201580003042.3.

* cited by examiner

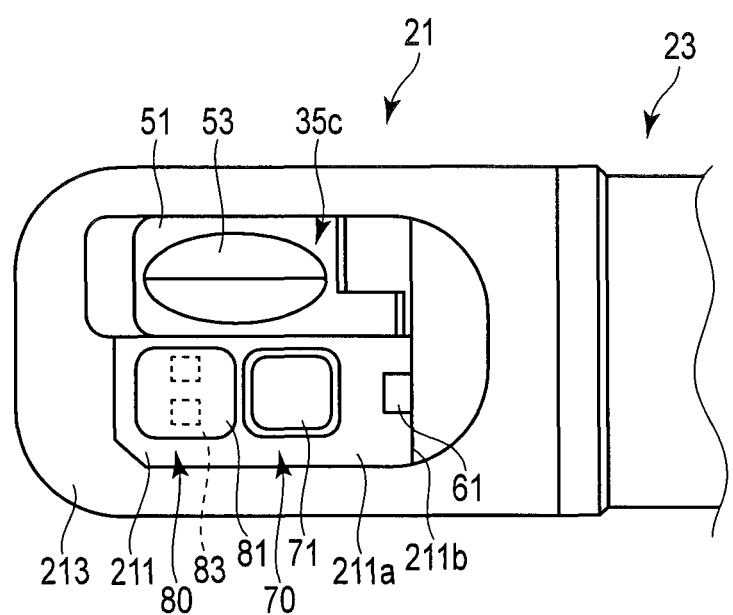
F I G. 1B

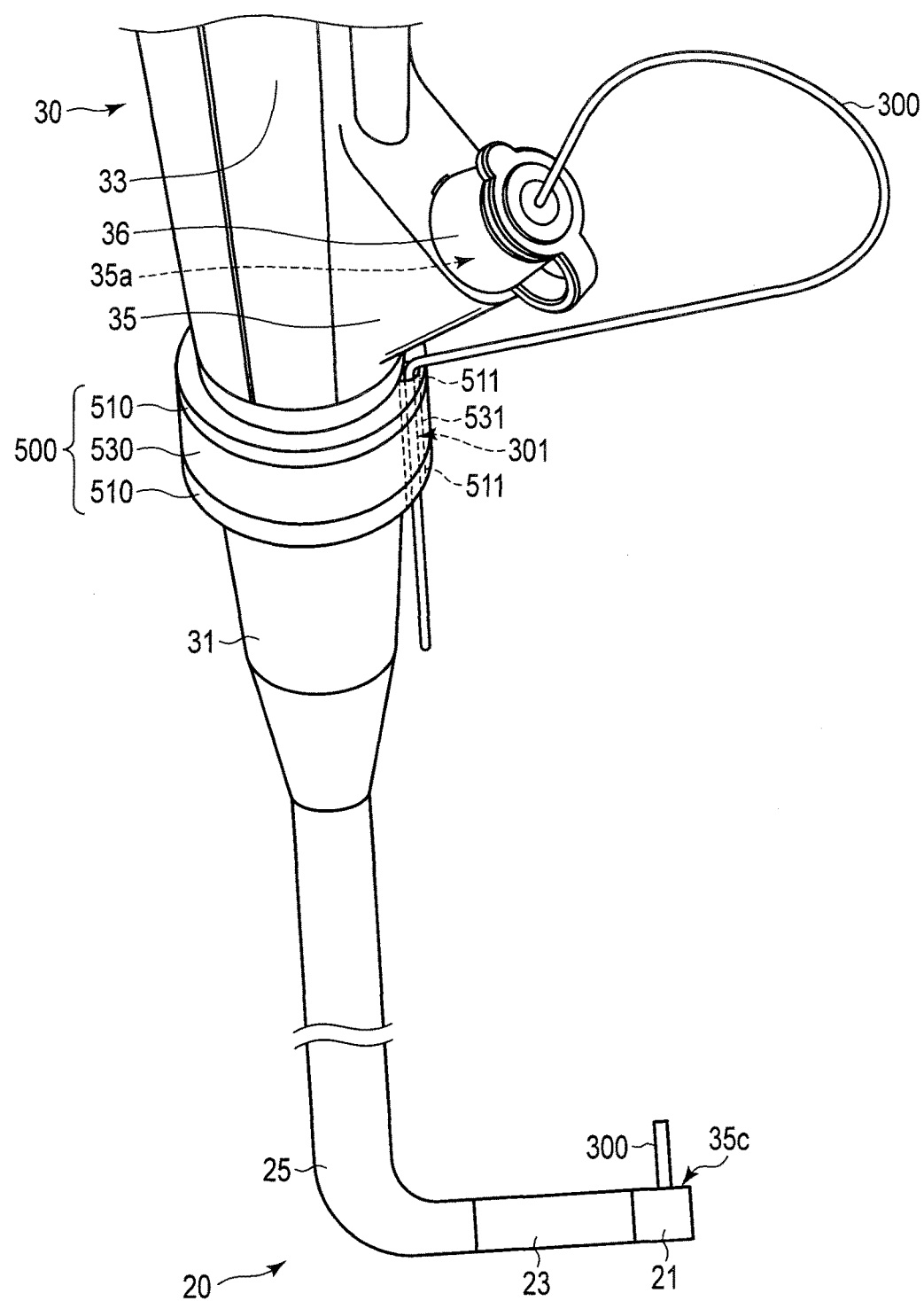
F I G. 2A

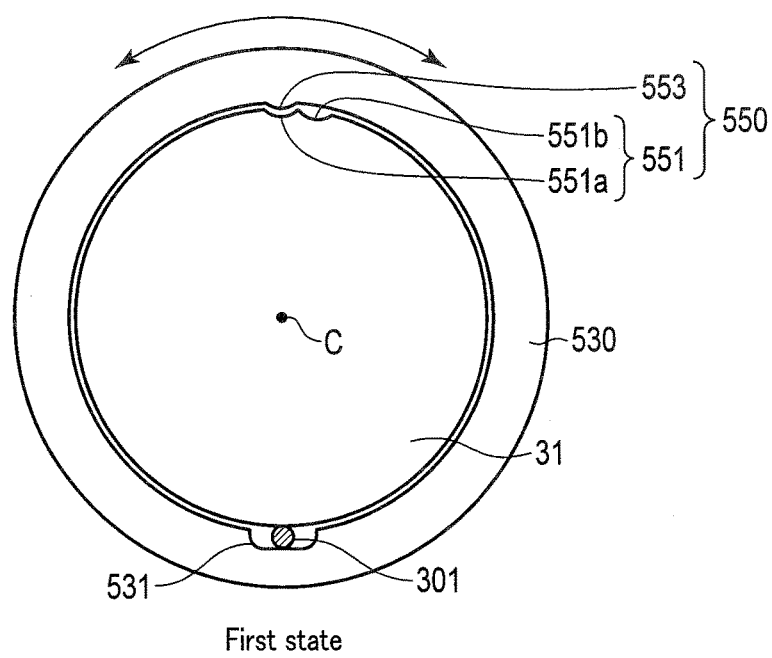
F I G. 3A
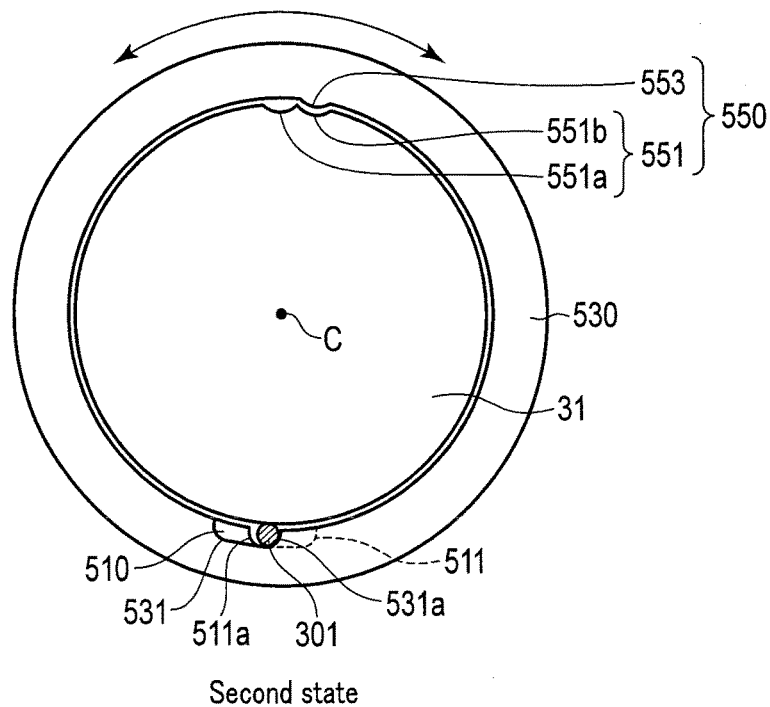
F I G. 3B

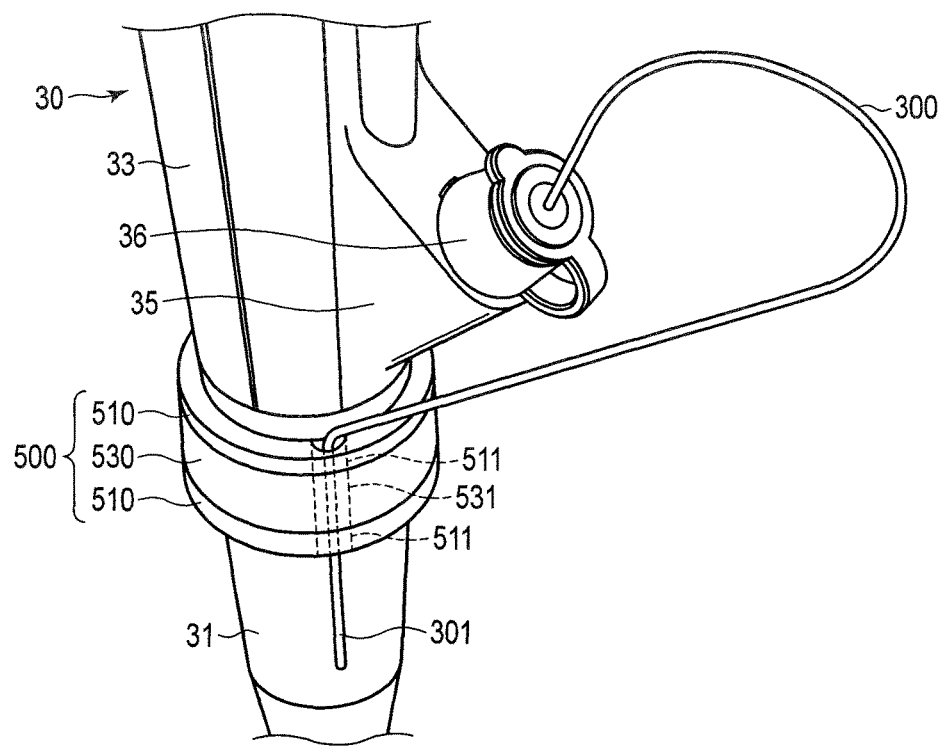
F I G. 5
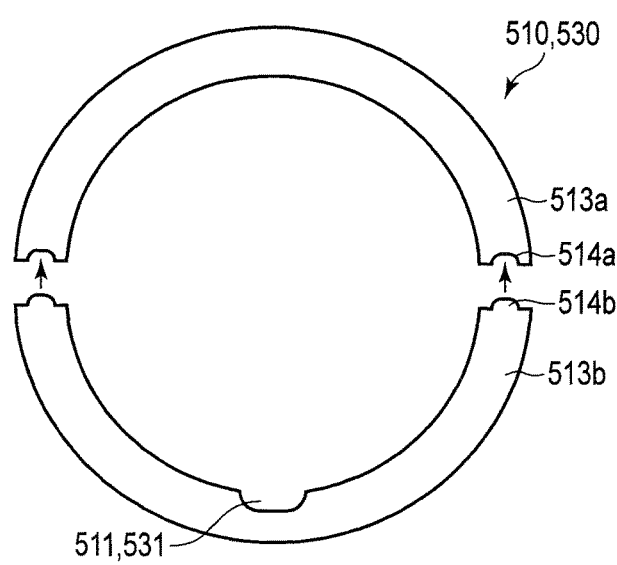
F I G. 6A

First state

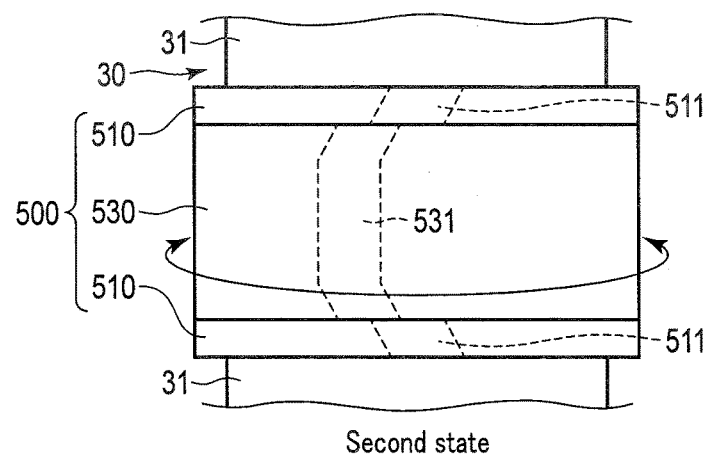
Second state
F I G. 8B
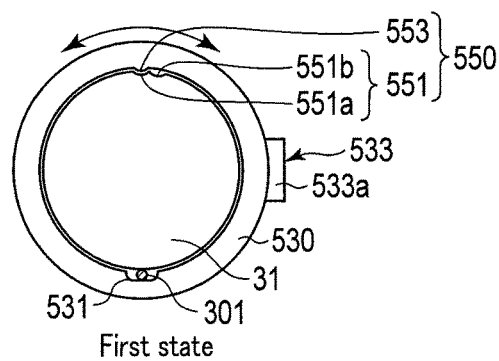
First state
F I G. 9A
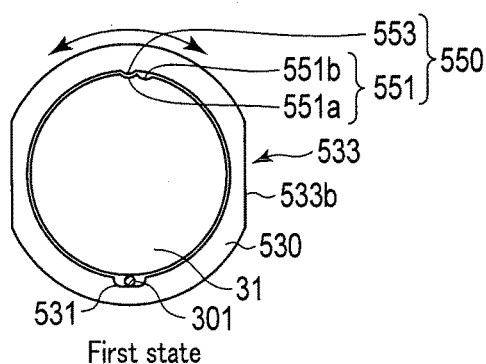
First state
F I G. 9B

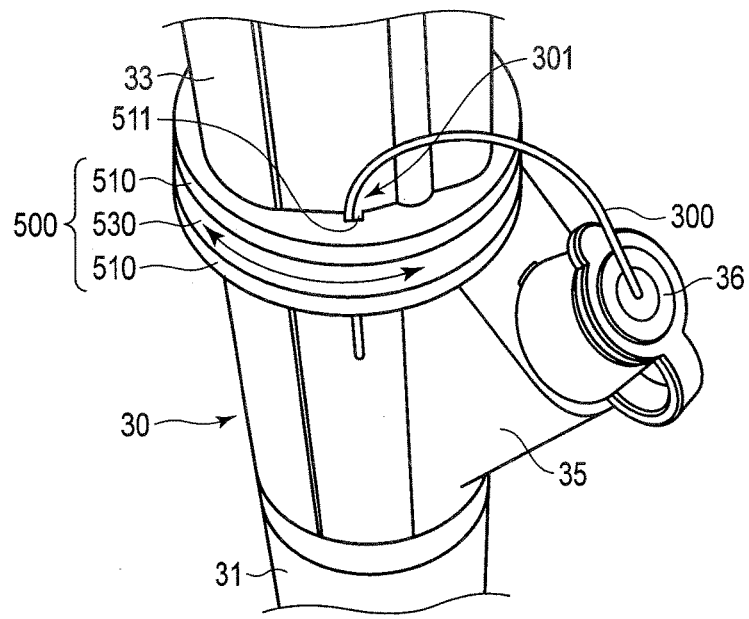
F I G. 10B
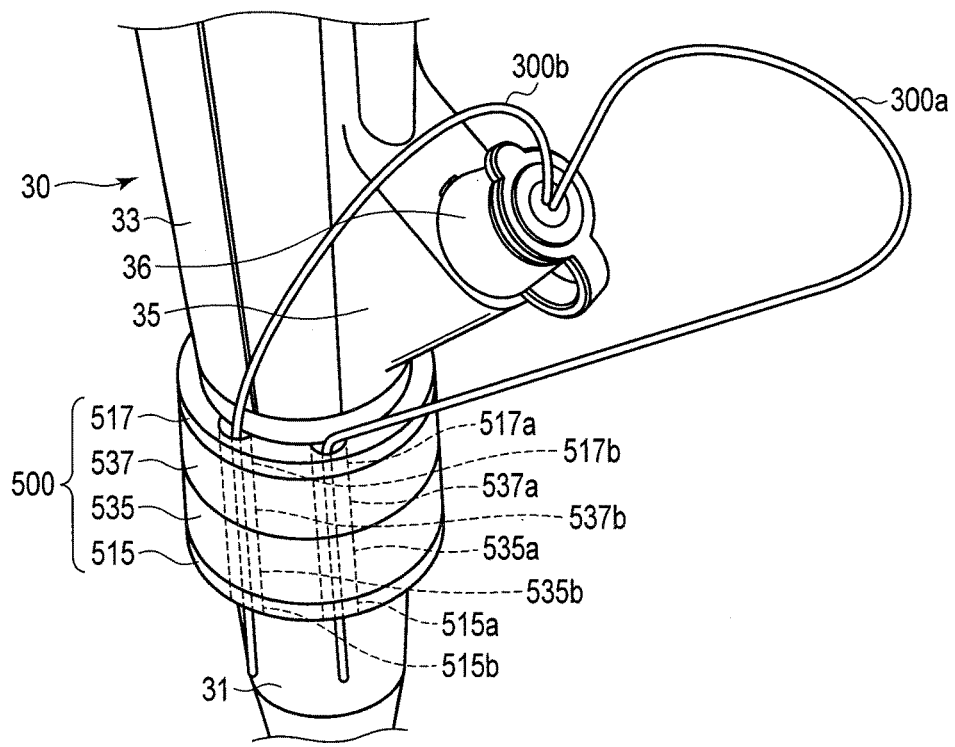
F I G. 11A

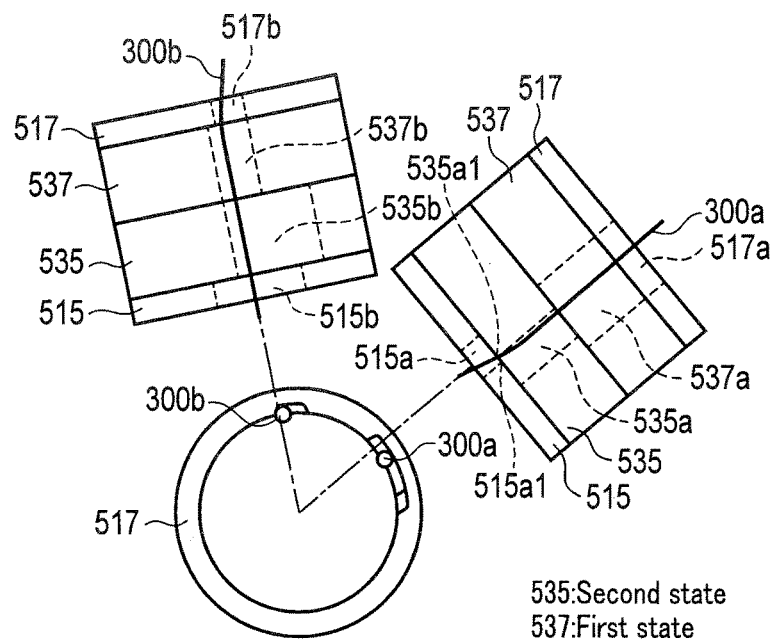
F I G. 11E
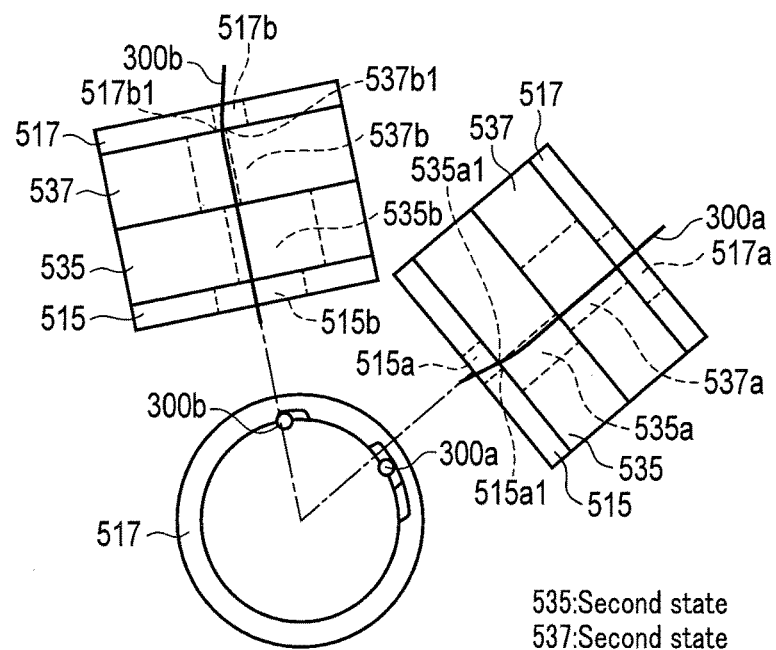
F I G. 11F

HOLDING MECHANISM FOR ENDOSCOPE GUIDE MEMBER, AND ENDOSCOPE

CROSS-REFERENCE TO RELATED APPLICATIONS

This application is a Continuation Application of PCT Application No. PCT/JP2015/059975, filed Mar. 30, 2015 and based upon and claiming the benefit of priority from prior Japanese Patent Application No. 2014-089652, filed Apr. 23, 2014, the entire contents of all of which are incorporated herein by reference.

BACKGROUND OF THE INVENTION

1. Field of the Invention

The present invention relates to a holding mechanism for an endoscope guide member to hold the endoscope guide member that guides a treatment instrument protruding from a distal end opening portion of an endoscope to a subject, and an endoscope which has this holding mechanism.

2. Description of the Related Art

In general, when a treatment instrument treats a subject such as a bile duct, a side-viewing endoscope and a guide member which guides the treatment instrument to the subject are used.

In this case, the treatment instrument has a cylindrical member through which the guide member can be inserted. The guide member is made of, for example, a thin linear member. The guide member is inserted through the cylindrical member and maintains, for example, the position of a distal end portion of the guide member, thereby the treatment instrument can move along the guide member.

The guide member is inserted, via a treatment instrument insertion hole portion, into a treatment instrument insertion channel which is in communication with the treatment instrument insertion hole portion from a forceps plug portion provided in a grasp portion of the endoscope. The distal end portion of the guide member is then inserted through the treatment instrument insertion channel, and protrudes from the distal end opening portion provided at a distal end portion of the endoscope insertion portion. In the side-viewing endoscope, the distal end portion of the guide member protrudes to a lateral side of the distal end portion of the insertion portion. The distal end portion of the guide member then reaches the subject.

The treatment instrument moves along the guide member by the cylindrical member so that the guide member passes through the guide member. In this instance, the treatment instrument is guided by the guide member, and then inserted into the treatment instrument insertion channel from the forceps plug portion via the treatment instrument insertion hole portion. The treatment instrument is then guided by the guide member, inserted through the treatment instrument insertion channel, protrudes to the lateral side from the distal end opening portion, and reaches the subject. In this way, the treatment instrument is guided to the subject by the guide member.

Such guide members are disclosed in, for example, Jpn. PCT. National Publication No. 2008-529723, Jpn. Pat. Appln. KOKAI Publication No. 2001-340468, and Jpn. PCT. National Publication No. 2001-511023. In Jpn. PCT. National Publication No. 2008-529723, Jpn. Pat. Appln. KOKAI Publication No. 2001-340468, and Jpn. PCT. National Publication No. 2001-511023, a proximal end portion of the guide member is held by a holding member separate from the endoscope so that the guide member is fixed and the displacement of the guide member is prevented. The holding member is attached to the treatment instrument insertion hole portion so that the holding member is attached detachably from the endoscope.

BRIEF SUMMARY OF THE INVENTION

An aspect of a holding mechanism for an endoscope guide members of the invention holds the endoscope guide member which guides a treatment instrument, the endoscope guide member being inserted into a lumen through an insertion portion which is inserted into the lumen, and being movable in an axial direction of the insertion portion relative to an opening portion provided in the insertion portion, includes a fixed holding portions which hold a part of a proximal end side of the endoscope guide member exposed from the endoscope at an operation portion of the endoscope coupled to a proximal end portion of the insertion portion; and a rotary holding portions which switch the holding state of the holding mechanism by rotation to either a first state in which the rotary holding portion holds, together with the fixed holding portion, a the part of the proximal end side of the endoscope guide member exposed from the endoscope at the operation portion, or the second state in which the rotary holding portion fixes, together with the fixed holding portion, a part of the proximal end side of the endoscope guide member exposed from the endoscope.

An aspect of an endoscope of the invention includes the holding mechanism described above.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1B is a top view of a distal end hard portion;

FIG. 2A is a schematic diagram of a holding mechanism according to the first embodiment;

FIG. 3A is a diagram showing a first state in a positioning mechanism;

FIG. 3B is a diagram showing a second state in the positioning mechanism;

FIG. 5 is a diagram showing an example of the arrangement positions of a fixed-side insertion portion and a rotary-side insertion portion;

FIG. 6A is a diagram showing an example of the attachment and detachment of a fixed holding portion and a rotary holding portion, and showing a separation type;

FIG. 8B is a diagram showing that the first state shown in FIG. 8A has been switched to the second state;

FIG. 9A is a diagram showing an example of an operation portion which operates the rotary holding portion;

FIG. 9B is a diagram showing an example of the operation portion which operates the rotary holding portion;

FIG. 10B is a perspective view showing an example of the arrangement position of the holding mechanism, and showing the part around the holding mechanism which is provided in a grasp portion;

FIG. 11A is a schematic diagram of a holding mechanism according to a second embodiment;

FIG. 11E is a diagram illustrating that one rotary holding portion is in the second state and that the other rotary holding portion is in the first state;

FIG. 11F is a diagram illustrating that both of the rotary holding portions are in the second state.

DETAILED DESCRIPTION OF THE INVENTION

Hereinafter, embodiments of the present invention will be described in detail with reference to the drawings.

The first embodiment is described with reference to FIG. 1A, FIG. 1B, FIG. 2A, FIG. 2B, FIG. 2C, FIG. 3A, FIG. 3B, FIG. 4A, FIG. 4B, FIG. 4C, and FIG. 4D. Some components are not shown in some drawings for clarity of the drawings; for example, a holding mechanism 500 is not shown in FIG. 1A.

[Endoscope 10]

Figure 1A:
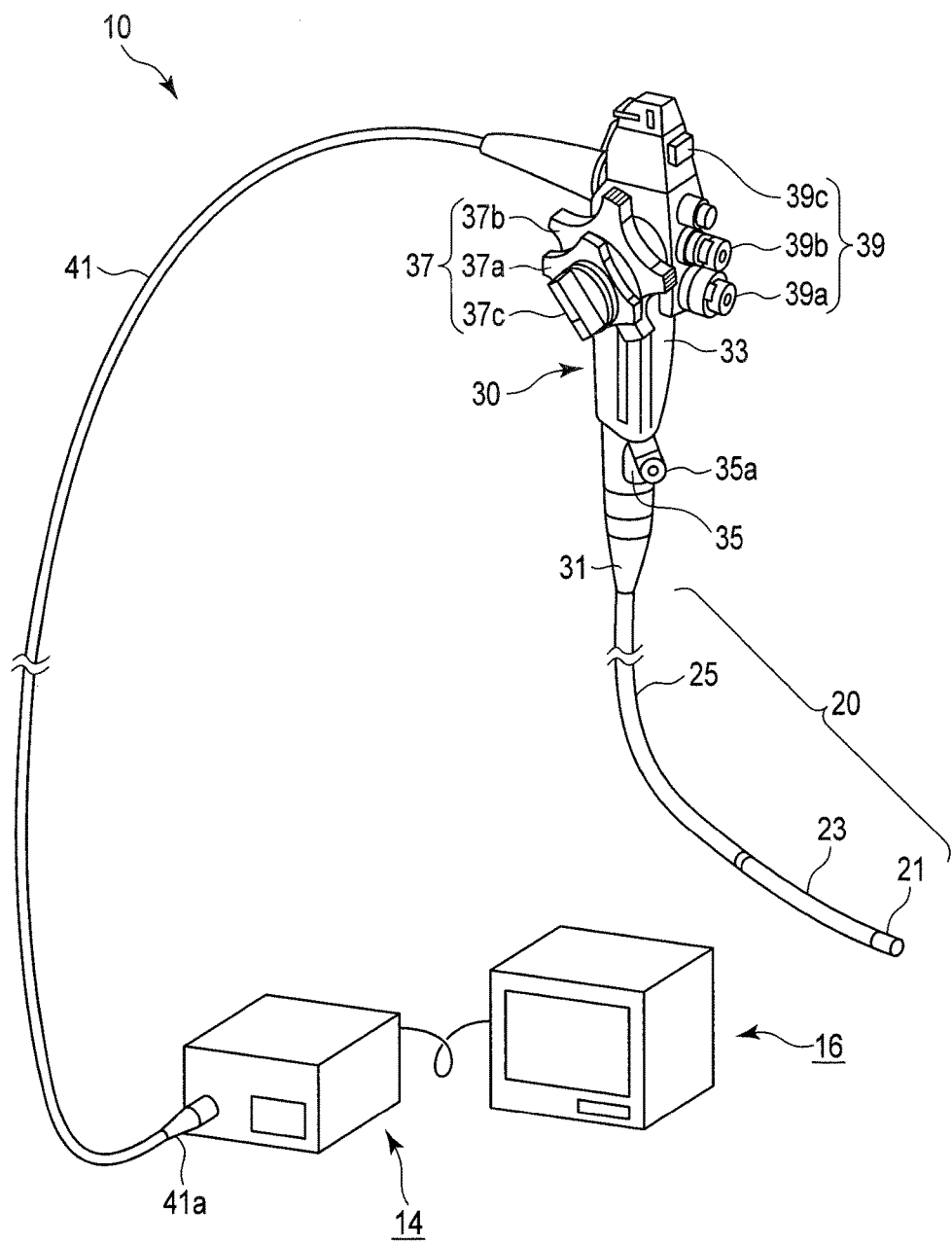
FIG. 1A is a schematic perspective view of a side-viewing endoscope according to a first embodiment of the present invention.

An endoscope 10 shown in FIG. 1A is, for example, a side-viewing endoscope.

As shown in FIG. 1A, the endoscope 10 has a hollow elongated insertion portion 20 which is inserted into a lumen such as a body cavity of a patient, and an operation portion 30 which is coupled to a proximal end portion of the insertion portion 20 and which operates the endoscope 10.

[Insertion Portion 20]

As shown in FIG. 1A, the insertion portion 20 has a distal end hard portion 21, a bending portion 23, and a flexible tubular portion 25 from a distal end portion side of the insertion portion 20 toward the proximal end portion side of the insertion portion 20. A proximal end portion of the distal end hard portion 21 is coupled to a distal end portion of the bending portion 23, and a proximal end portion of the bending portion 23 is coupled to a distal end portion of the flexible tubular portion 25.

The distal end hard portion 21 is the distal end portion of the insertion portion 20, and is hard and unbendable. The configuration of the distal end hard portion 21 will be described later.

The bending portion 23 bends in a desired direction such as an upward, downward, rightward, or leftward direction by an operation of a later-described bending operation portion 37. The bending section 23 bends, whereby a position and a direction of the distal end hard portion 21 are changed. An observation target is then illuminated by unshown illumination light, and the observation target is brought into an observation field. This observation target is, for example, an affected part or a lesion in a subject (e.g., body cavity).

The flexible tubular portion 25 has desired flexibility. Therefore, the flexible tubular portion 25 is bent by external force. The flexible tubular portion 25 is a tubular member extending from a later-described body portion 31 in the operation portion 30.

[Operation Portion 30]

As shown in FIG. 1A, the operation portion 30 has the body portion 31 from which the flexible tubular portion 25 extends, a grasping portion 33 which is coupled to a proximal end portion of the body portion 31 and which is grasped by an operator who operates the endoscope 10, and a universal cord 41 which is connected to the grasping portion 33.

[Grasping Portion 33]

As shown in FIG. 1A, the grasping portion 33 has a treatment instrument insertion portion 35, the bending operation portion 37 which operates to bend the bending portion 23, and a switch portion 39. The treatment instrument insertion portion 35 is provided on a distal end portion side of the grasping portion 33, the bending operation portion 37 and the switch portion 39 are provided on a proximal end portion side of the grasping portion 33.

[Treatment Instrument Insertion Portion 35]

As shown in FIG. 1A, the treatment instrument insertion portion 35 branches off from the grasping portion 33. Thus, a central axis direction of the treatment instrument insertion portion 35 is slanted relative to a central axis direction of the grasping portion 33.

As shown in FIG. 1A, the treatment instrument insertion portion 35 has a treatment instrument insertion hole portion 35a which is provided at the end portion of the treatment instrument insertion portion 35 and which is used to insert an endoscope guide member 300 and a treatment instrument 400 that will be described later into the endoscope 10.

The treatment instrument insertion hole portion 35a is coupled to a proximal end portion of an unshown treatment instrument insertion channel. The treatment instrument insertion channel is provided inside the insertion portion 20, and provided from the flexible tubular portion 25 to the distal end hard portion 21 via the bending portion 23. A distal end portion of the treatment instrument insertion channel is in communication with a distal end opening portion 35c (see FIG. 1B) provided in the distal end hard portion 21. The treatment instrument insertion hole portion 35a is an insertion hole portion used to insert the guide member 300 and the treatment instrument 400 into the treatment instrument insertion channel.

As shown in FIG. 1A, a central axis of the treatment instrument insertion hole portion 35a is provided coaxially with the central axis of the treatment instrument insertion portion 35, and is thus slanted relative to the central axis of the grasping portion 33. A central axis direction is slanted relative to the central axis direction of the grasping portion 33.

As shown in FIG. 2A, the treatment instrument insertion portion 35 further has a cylindrical forceps plug portion 36 to be provided in the treatment instrument insertion portion 35. The forceps plug portion 36 is made of, for example, a resin such as rubber. A central axis of the forceps plug portion 36 is provided coaxially with the central axis of the treatment instrument insertion hole portion 35a. Thus, the forceps plug portion 36 is slanted relative to the grasping portion 33. When the forceps plug portion 36 is provided in the treatment instrument insertion portion 35, the forceps plug portion 36 is in communication with the treatment instrument insertion channel via the treatment instrument insertion hole portion 35a.

Figure 4A:
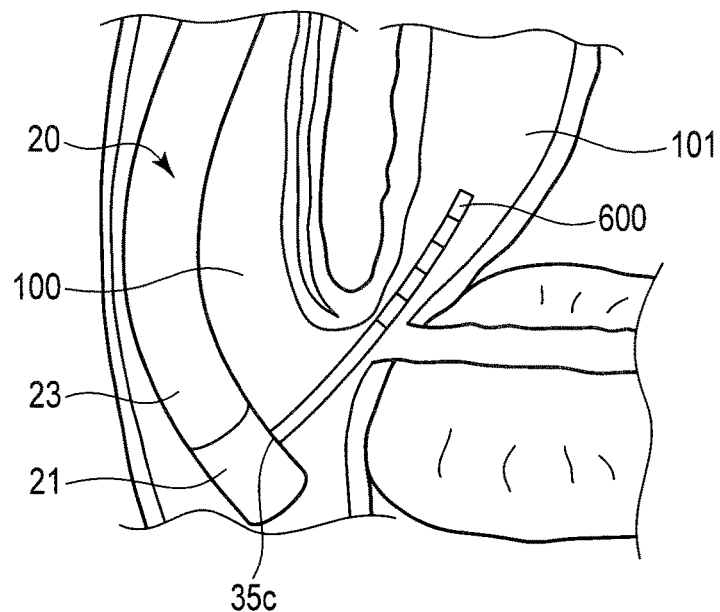
FIG. 4A is a diagram illustrating how a contrast tube is inserted into a bile duct.
Figure 4B:
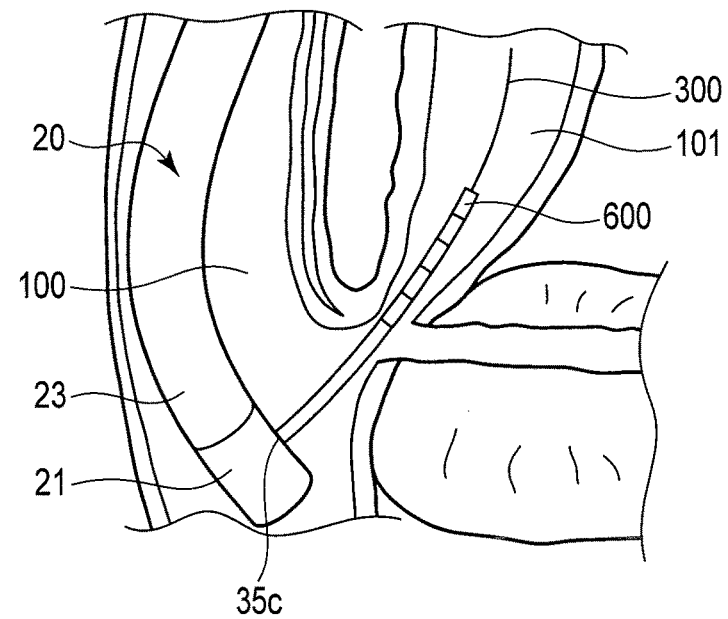
FIG. 4B is a diagram illustrating how a guide member is inserted into the bile duct.
Figure 4C:
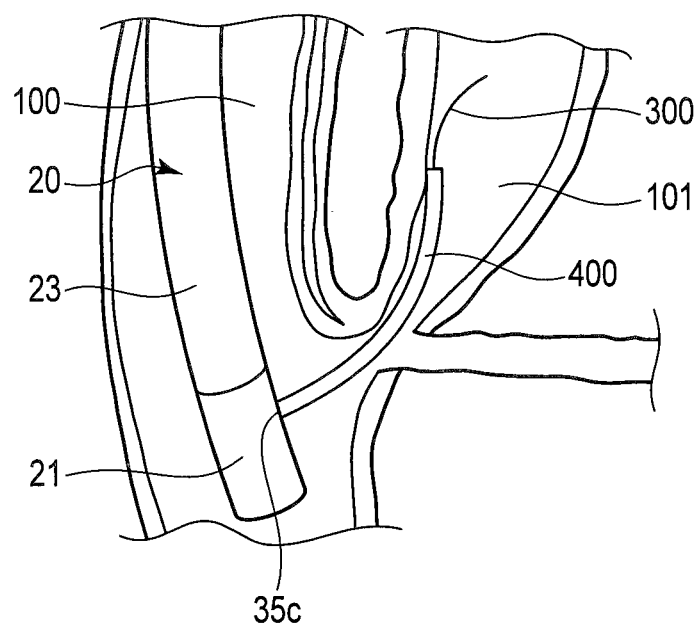
FIG. 4C is a diagram illustrating how a treatment instrument is inserted into the bile duct under the guidance of the guide member.

The guide member 300 shown in FIG. 2A and the treatment instrument 400 shown in FIG. 4C are inserted into the treatment instrument insertion channel from the forceps plug portion 36 via the treatment instrument insertion hole portion 35a, and pressed into the side of the distal end hard portion 21. As shown in FIG. 4B and FIG. 4C, the guide member 300 and the treatment instrument 400 are then protruded from the distal end opening portion 35c.

[Bending Operation Portion 37]

As shown in FIG. 1A, the bending operation portion 37 has a horizontal bending operation knob 37a, a vertical bending operation knob 37b, and a fixing knob 37c.

[Switch Portion 39]

As shown in FIG. 1A, the switch portion 39 has a suction switch 39a, an air/water supply switch 39b, and various switches 39c for endoscopic photography.

[Universal Cord 41]

As shown in FIG. 1A, the universal cord 41 is extended from a side surface of the grasping portion 33. The universal cord 41 has a connector 41a which can be attached to and removed from a control device 14. The control device 14 controls the endoscope 10. The control device 14 has an image processing section which processes images taken by an imaging unit. The control device 14 is connected to a monitor 16 which is a display section for displaying the images taken by the imaging unit.

[Configuration of Distal End Hard Portion 21]

As shown in FIG. 1B, the distal end hard portion 21 has a body portion 211 and a cap portion 213.

The body portion 211 is made of a metal such as stainless steel. A proximal end portion of the body portion 211 is coupled to the distal end portion of the bending portion 23. The body portion 211 has, for example, a circular cylindrical shape. As shown in FIG. 1B, a part of an outer circumferential surface of the body portion 211 is formed into a flat shape by cutting out a part of the body portion 211. Thus, the body portion 211 has a flat portion 211a, and a wall surface portion 211b which intersects at right angles with the flat portion 211a.

As shown in FIG. 1B, the cap portion 213 covers the body portion 211 except for the flat portion 211a and the wall surface portion 211b. The cap portion 213 is water-tightly bonded to the body portion 211. The cap portion 213 is fixed to the body portion 211. The cap portion 213 has electric insulating properties.

[Body Portion 211]

As shown in FIG. 1B, the distal end opening portion 35c, an air/water supply nozzle 61, an imaging unit 70, and an illumination unit 80 are mounted on the body portion 211.

[Distal End Opening Portion 35c]

As shown in FIG. 1B, the distal end opening portion 35c is depressed in the flat portion 211a, and is open to a lateral side of the body portion 211. The distal end opening portion 35c houses a treatment instrument raising base 51 which can be remotely operated to swing in response to a raising operation at hand. The treatment instrument raising base 51 is swung in response to the raising operation, and guides the treatment instrument 400 to protrude from the distal end opening portion 35c to the lateral side of the body portion 211. The treatment instrument raising base 51 may have a treatment instrument guide groove portion 53 which guides the treatment instrument 400 from the body portion 211 to an outside. The treatment instrument guide groove portion 53 is provided in a center portion of the treatment instrument raising base 51, and further provided along the longitudinal direction of the treatment instrument raising base 51.

[Air/Water Supply Nozzle 61]

As shown in FIG. 1B, the air/water supply nozzle 61 is provided in the wall surface portion 211b. The air/water supply nozzle 61 is provided in alignment with an observation window 71 of the imaging unit 70 in the axial direction of the insertion portion 20 so that the air/water supply nozzle 61 supplies air or water to the observation window 71 of the imaging unit 70. When the air/water supply switch 39b is operated, the air/water supply nozzle 61 supplies air or water to the observation window 71.

[Imaging Unit 70]

As shown in FIG. 1B, the imaging unit 70 has the observation window 71, an unshown prism, and an unshown imaging portion.

[Observation Window 71]

As shown in FIG. 1B, reflected light which has been reflected from the observation target enters the observation window 71 in a side-viewing observation. Thus, the observation window 71 is provided in a circumferential surface of the body portion 211, for example, the flat portion 211a, and is provided flush with the flat portion 211a.

[Prism]

The unshown prism reflects the reflected light which has transmitted through the observation window 71, and thus varies the travel of the reflected light. The prism is provided inside the body portion 211 so that a central axis of the prism is provided substantially coaxially with a central axis of the observation window 71.

[Imaging Portion]

The unshown imaging portion is provided so that the imaging portion is adjacent to the prism in a axial direction of the insertion portion 20. That is, the imaging portion is provided substantially in alignment with the prism in the axial direction of the insertion portion 20. The imaging portion is provided along the axial direction of the insertion portion 20 together with the prism. Such an imaging portion is provided inside the body portion 211 to face the prism.

[Illumination Unit 80]

As shown in FIG. 1B, the illumination unit 80 has an illumination window 81, illumination portions 83, and unshown illumination cables connected to the illumination portions 83. The illumination unit 80 is provided separately from the imaging unit 70.

[Illumination Window 81]

As shown in FIG. 1B, the illumination window 81 transmits the illumination light applied to the observation target in the side-viewing observation. Thus, the illumination window 81 is provided in the circumferential surface of the body portion 211, for example, the flat portion 211a, and is provided flush with the flat portion 211a. The illumination window 81 is provided so that the illumination window 81 is adjacent to the observation window 71 in the axial direction of the insertion portion 20. The illumination window 81 is provided, for example, closer to the distal end portion side of the body portion 211 than the observation window 71. A central axis of the illumination window 81 is provided along an orthogonal direction.

[Illumination Portions 83]

The illumination portions 83 emit illumination light such as white light in an upward direction which is a lateral direction. The illumination portions 83 are illumination light emitting ends such as light guides which guide illumination light from a light source, or light emitting elements such as LEDs. For example, two illumination portions 83 are provided.

As shown in FIG. 1B, the illumination portions 83 are provided inside the body portion 211. The illumination portions 83 are provided under the illumination window 81.

[Illumination Cables]

The unshown illumination cable is provided for each of the illumination portions 83. The illumination cables are inserted through the connector 41a via the bending portion 23, the flexible tubular portion 25, the operation portion 30, and the universal cord 41. When the connector 41a is connected to the control device 14, the illumination cables are connected to the control device 14, and electric power for the illumination portions 83 to emit the illumination light is supplied to the illumination cables. The illumination cables then supply the electric power to the illumination portions 83.

[Guide Member 300, Treatment Instrument 400, and Endoscope Guide Member Holding Mechanism]

As shown in FIG. 2A, FIG. 2B, FIG. 2C, FIG. 4A, FIG. 4B, FIG. 4C, and FIG. 4D, the endoscope 10 is used together with the guide member 300 and the treatment instrument 400 which are separate from the endoscope 10. The endoscope 10 further has an endoscope guide member holding mechanism (hereinafter referred to as a holding mechanism 500) for holding the guide member 300 which is inserted into the treatment instrument insertion channel inside the endoscope 10 from the forceps plug portion 36 (the treatment instrument insertion hole portion 35a) before the treatment instrument 400, protrudes from the distal end opening portion 35c, reaches the subject, and then guides the treatment instrument 400 to the subject. The holding mechanism 500 holds the guide member 300 which guides the treatment instrument 400. The guide member 300 is inserted into the lumen through the insertion portion 20 of the endoscope 10 which is inserted into the lumen, and can be moved in the axial direction of the insertion portion 20 relative to the distal end opening portion 35c provided at the distal end portion of the insertion portion 20.

[Guide Member 300]

As shown in FIG. 2A, FIG. 4B, and FIG. 4C, the guide member 300 is inserted into the treatment instrument insertion channel from the forceps plug portion 36 via the treatment instrument insertion hole portion 35a. A distal end portion of the guide member 300 is then inserted through the treatment instrument insertion channel, and protrudes from the distal end opening portion 35c provided in the side surface of the distal end portion of the insertion portion 20. Since the distal end opening portion 35c is provided in the side surface, the distal end portion of the guide member 300 protrudes to the lateral side of the distal end portion of the insertion portion 20. The distal end portion of the guide member 300 then reaches the subject. A proximal end portion 301 of the guide member 300 is exposed to the outside of the endoscope 10 from the forceps plug portion 36 while the distal end portion of the guide member 300 is protruding from the distal end opening portion 35c.

The guide member 300 is inserted into the treatment instrument insertion channel from the forceps plug portion 36 before the treatment instrument 400 is inserted into the treatment instrument insertion channel from the forceps plug portion 36. Although described later in detail, the guide member 300 guides the treatment instrument 400 to the subject while the guide member 300 is inserted into the treatment instrument insertion channel and the distal end portion of the guide member 300 is exposed to the outside from the distal end opening portion 35c.

Such a guide member 300 is made of, for example, a thin linear member. The linear member has, for example, stainless steel wires. The linear member may have, for example, nickel-titanium wires having surfaces coated with a fluorine resin.

[Treatment Instrument 400]

As shown in FIG. 4C, the treatment instrument 400 is used, for example, to treat a subject such as a bile duct 101. Such a treatment instrument 400 has, for example, a knife for endoscopic sphincterotomy (hereinafter, EST). The treatment instrument 400 is made of, for example, a thin linear member.

Figure 4D:
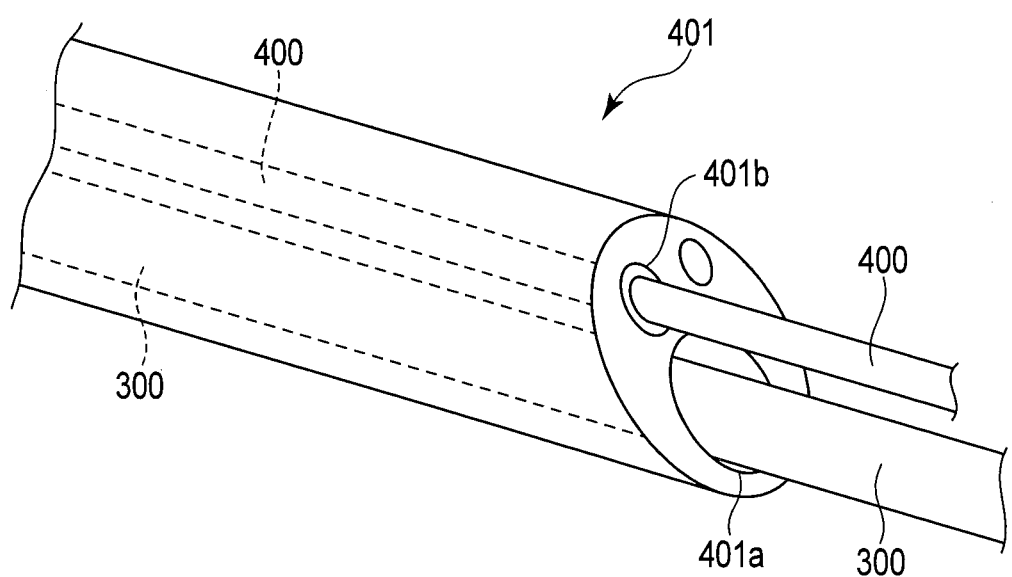
FIG. 4D is a perspective view of a cylindrical member through which the guide member is inserted.

As shown in FIG. 4D, the treatment instrument 400 is used together with a cylindrical member 401. The cylindrical member 401 functions as, for example, a multi-lumen. The cylindrical member 401 has an insertion hole portion 401a into which the guide member 300 can be inserted, and an engagement hole portion 401b with which, for example, the distal end portion of the treatment instrument 400 engages. The cylindrical member 401 can slide on the guide member 300 while the guide member 300 is inserted through the insertion hole portion 401a. As a result of this sliding, the cylindrical member 401 functions as a monorail portion, thereby the treatment instrument 400 can move along the guide member 300. In this instance, the treatment instrument 400 is guided by the guide member 300, and then inserted into the treatment instrument insertion channel from the forceps plug portion 36 via the treatment instrument insertion hole portion 35a. The treatment instrument 400 is then guided by the guide member 300, and thus inserted through the treatment instrument insertion channel, protrudes to the lateral side from the distal end opening portion 35c, and reaches the subject.

Thus, the treatment instrument 400 is guided to the subject by the guide member 300.

[Holding Mechanism 500]

In general, the treatment instrument 400 moves backward and forward along the axial direction of the treatment instrument 400 by a right-hand operation of a surgeon while the grasping portion 33 is grasped with a left hand of the surgeon. Thus, the holding mechanism 500 is provided in the operation portion 30, although described later in detail, the holding mechanism 500 can hold a proximal end portion 301 of the guide member 300 or release holding of the proximal end portion 301 by the right-hand operation of the surgeon while the grasping portion 33 is grasped with the left hand of the surgeon. In other words, the proximal end portion 301 of the guide member 300 can be attached to or detached from the grasping portion 33 via the holding mechanism 500 by the right-hand operation of the surgeon while the grasping portion 33 is grasped with the left hand of the surgeon. Thus, in the operation portion 30, the holding mechanism 500 is provided at the position where the holding mechanism 500 does not interrupt the left-hand operation of the surgeon who operates the endoscope 10 and at the position where the holding mechanism 500 can be operated by the right-hand operation. As shown in FIG. 2A, the holding mechanism 500 is provided, for example, lower than the treatment instrument insertion portion 35, more specifically, provided in the body portion 31. The holding mechanism 500 is provided so that fixed-side insertion portions 511 and a rotary-side insertion portion 531 that will be described later are provided lower than the treatment instrument insertion portion 35 in a central axis direction of the endoscope 10 and provided in alignment with the treatment instrument insertion portion 35.

Figure 2B:
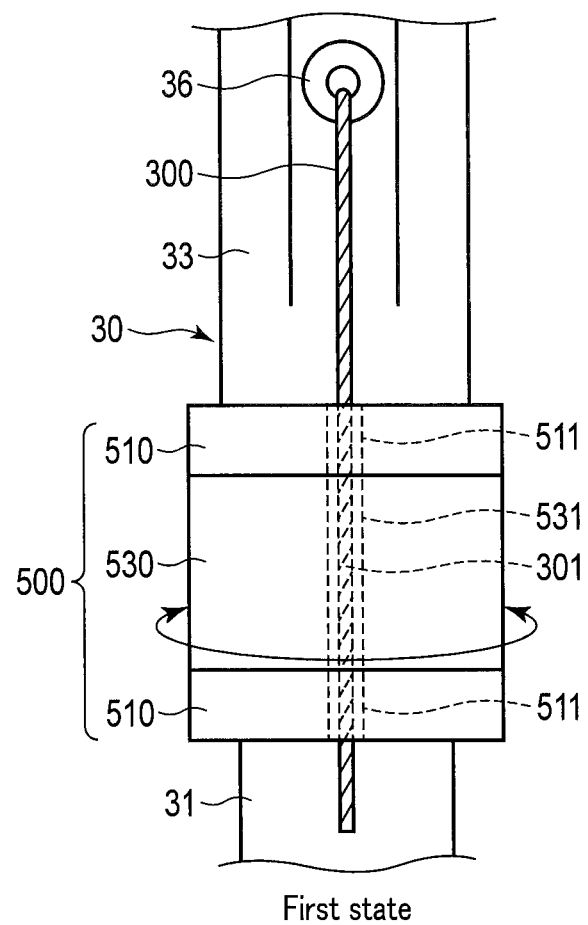
FIG. 2B is a diagram showing a first state in the holding mechanism.

As shown in FIG. 2A, FIG. 4B, and FIG. 4C, the holding mechanism 500 which is provided as above holds the guide member 300 which reaches the subject as described above to guide the treatment instrument 400 to the subject when the treatment instrument 400 is inserted into the treatment instrument insertion channel inside the endoscope 10 from the forceps plug portion 36 (the treatment instrument insertion hole portion 35a) provided in the operation portion 30 of the endoscope 10 and protrudes from the distal end opening portion 35c provided at the distal end portion of the insertion portion 20 of the endoscope 10 to treat the subject. Specifically, as shown in FIG. 2A, FIG. 2B, and FIG. 2C, when the holding mechanism 500 holds the proximal end portion 301 of the guide member 300 which is exposed to the outside of the endoscope 10 from the forceps plug portion 36, the guide member 300 moves relative to the holding mechanism 500 while being held by the holding mechanism 500 and is thereby prevented from coming off the holding mechanism 500, or the guide member 300 is fixed to the holding mechanism 500 and the displacement of the guide member 300 is prevented.

Figure 2C:
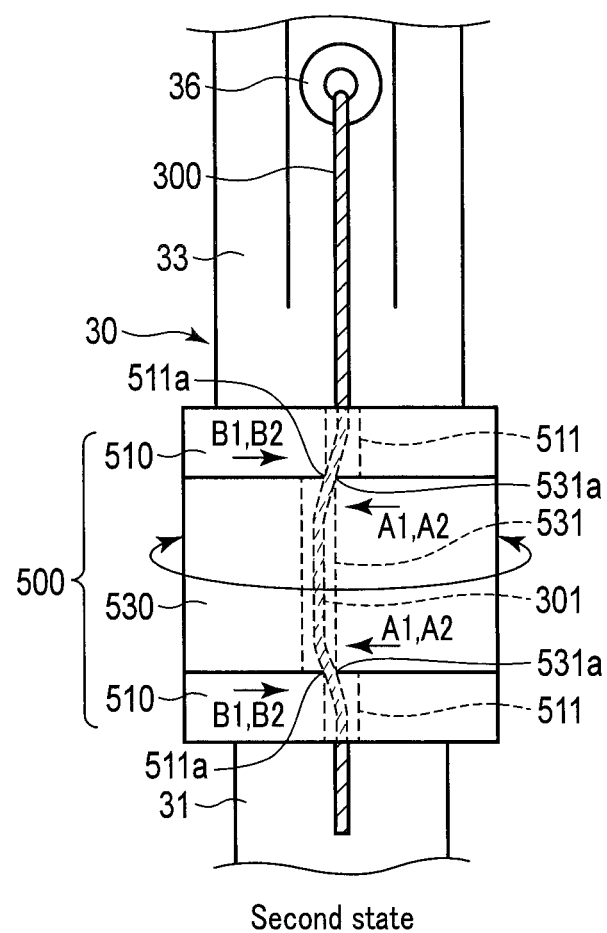
FIG. 2C is a diagram showing a second state in the holding mechanism.

Thus, as shown in FIG. 2A, FIG. 2B, and FIG. 2C, the holding mechanism 500 has fixed holding portions 510 which are detachably fixed to the operation portion 30, and a rotary holding portion 530 which is detachably provided in the operation portion 30. A central axes of the fixed holding portions 510 are coaxial with a central axis of the rotary holding portion 530, and are provided, for example, on a central axis C of the operation portion 30. A pair of fixed holding portions 510 are provided so that the fixed holding portions 510 sandwich the rotary holding portion 530 therebetween, for example, in a central axis direction of the body portion 31. In other words, the fixed holding portions 510 are provided at both end portions of the rotary holding portion 530 so that the fixed holding portions 510 are adjacent to the rotary holding portion 530 in the central axis direction of the body portion 31. The central axis of the body portion 31 is provided coaxially with the central axis of the grasping portion 33 which is the central axis C of the operation portion 30.

[Fixed Holding Portions 510]

The fixed holding portions 510 have, for example, a cylindrical shape, specifically, a circular cylindrical shape. As shown in FIG. 2A and FIG. 2B, the fixed holding portions 510 hold the proximal end portion 301 of the guide member 300 which is exposed to the outside of the endoscope 10 from the forceps plug portion 36 so that the guide member 300 can move along the axial direction of the guide member 300 while the distal end portion of the guide member 300 is protruding from the distal end opening portion 35c. In other words, the fixed holding portions 510 hold a part of the proximal end side of the guide member 300 exposed from the endoscope 10 to the operation portion 30 which operates the endoscope 10 and which is coupled to the proximal end portion of the insertion portion 20.

Thus, as shown in FIG. 2A, FIG. 2B, and FIG. 2C, each of the fixed holding portions 510 has, for example, the fixed-side insertion portion 511 through which the proximal end portion 301 of the guide member 300 is inserted and which holds the guide member 300 by the insertion. The fixed-side insertion portion 511 may be a groove portion formed in an inner circumferential surface of each of the fixed holding portions 510 or may be a bore portion formed in a thick portion of each of the fixed holding portions 510. In this case, the groove portion is recessed toward an outer circumferential surface of each of the fixed holding portions 510 from the inner circumferential surface of each of the fixed holding portions 510. When the fixed holding portions 510 are provided in the operation portion 30, the groove portions are covered with an outer circumferential surface of the body portion 31. Such fixed-side insertion portions 511 function as pipelines through which the guide member 300 is inserted. When the guide member 300 is inserted through the fixed-side insertion portions 511, the guide member 300 is prevented from coming off the fixed holding portions 510. The fixed-side insertion portions 511 are provided, for example, linearly along the central axis direction of the fixed holding portions 510. The fixed-side insertion portions 511 penetrate the fixed holding portions 510 in the central axis direction of the fixed holding portions 510. The fixed holding portions 510 are provided in the body portion 31 so that the central axis direction of the fixed-side insertion portions 511 is provided along the central axis direction of the body portion 31.

The fixed holding portions 510 are detachably fixed to, for example, the outer circumferential surface of the body portion 31, and function as unrotatable fixed rings. As shown in FIG. 2A, FIG. 2B, and FIG. 2C, the fixed holding portions 510 are provided around a circumference of the body portion 31.

[Rotary Holding Portion 530]

As shown in FIG. 3A and FIG. 3B, the rotary holding portion 530 has, for example, a cylindrical shape, specifically, a circular cylindrical shape. The rotary holding portion 530 functions as a rotary ring. As shown in FIG. 2A, FIG. 2B, and FIG. 3A, the rotary holding portion 530 holds, together with the fixed holding portions 510, the proximal end portion 301 of the guide member 300 which is exposed to the outside of the endoscope 10 from the forceps plug portion 36 so that the guide member 300 can move along the axial direction of the guide member 300 while the distal end portion of the guide member 300 is protruding from the distal end opening portion 35c.

Thus, as shown in FIG. 2A, FIG. 2B, FIG. 2C, FIG. 3A, and FIG. 3B, the rotary holding portion 530 has, for example, the rotary-side insertion portion 531 through which the proximal end portion 301 of the guide member 300 is inserted and which holds the guide member 300 by the insertion. The rotary-side insertion portion 531 may be a groove portion formed in an inner circumferential surface of the rotary holding portion 530 or may be a bore portion formed in a thick portion of the rotary holding portion 530. In this case, the groove portion is recessed toward an outer circumferential surface of the rotary holding portion 530 from the inner circumferential surface of the rotary holding portion 530. When the rotary holding portion 530 is provided in the operation portion 30, the groove portion is covered with the outer circumferential surface of the body portion 31. Such a rotary holding portion 530 functions as a pipeline through which the guide member 300 is inserted. When the guide member 300 is inserted through the rotary-side insertion portion 531, the guide member 300 is prevented from coming off the rotary holding portion 530. The rotary-side insertion portion 531 is provided, for example, linearly along the central axis direction of the rotary holding portion 530. The rotary-side insertion portion 531 penetrate the rotary holding portion 530 in the central axis direction of the rotary holding portion 530. The rotary holding portion 530 is provided in the body portion 31 so that the central axis direction of the rotary-side insertion portion 531 is provided along the central axis direction of the body portion 31.

As shown in FIG. 2A, FIG. 2B, and FIG. 2C, a diameter of the rotary-side insertion portion 531 is substantially the same as a diameter of the fixed-side insertion portions 511, and substantially the same as a diameter of the guide member 300. For example, the rotary holding portion 530 is longer than the fixed holding portions 510. For example, the rotary holding portion 530 has the same thickness as those of the fixed holding portions 510 so that the outer circumferential surface of the rotary holding portion 530 is provided flush with the outer circumferential surfaces of the fixed holding portions 510. When the grasping portion 33 is grasped with the left hand, the rotary holding portion 530 is provided together with the fixed holding portions 510 so that the fixed-side insertion portions 511 and the rotary-side insertion portion 531 are located to be wrapped by a palm of the right hand. In this instance, as shown in FIG. 2A, FIG. 2B, and FIG. 2C, the rotary holding portion 530 and the fixed holding portions 510 are provided so that the fixed-side insertion portions 511 and the rotary-side insertion portion 531 are provided under, for example, the forceps plug portion 36, for example, substantially in alignment with the forceps plug portion 36.

The rotary holding portion 530 is detachably provided on, for example, the outer circumferential surface of the body portion 31. As shown in FIG. 2A, FIG. 2B, FIG. 2C, FIG. 3A, and FIG. 3B, the rotary holding portion 530 is provided around the circumference of the body portion 31.

As shown in FIG. 2A, FIG. 2C, and FIG. 3B, the rotary holding portion 530 fixes, together with the fixed holding portions 510, the proximal end portion 301 of the guide member 300 while the distal end portion of the guide member 300 is protruding from the distal end opening portion 35c. As a result, the guide member 300 is fixed, and the displacement of the guide member 300 is prevented. Thus, the rotary holding portion 530 is provided in, for example, the body portion 31, and can rotate around, for example, the central axis of the body portion 31. In this case, as shown in FIG. 2A, FIG. 2B, FIG. 2C, FIG. 3A, and FIG. 3B, the rotary holding portion 530 can rotate relative to the body portion 31 and the fixed holding portions 510. The rotary holding portion 530 is sandwiched between the fixed holding portions 510 as described above. Thus, the rotation of the rotary holding portion 530 is guided by the fixed holding portions 510. The rotary holding portion 530 is then positioned in the axial direction of the body portion 31 by the fixed holding portions 510.

As shown in FIG. 2A, FIG. 2B, FIG. 2C, FIG. 3A, and FIG. 3B, the rotary holding portion 530 is rotatable around the central axis C of the operation portion 30 so that the holding state of the holding mechanism 500 is switched to either a first state or a second state. The first state shows that the rotary holding portion 530 holds, together with the fixed holding portions 510, the proximal end portion 301 of the guide member 300 which is exposed to the outside of the endoscope 10 from the forceps plug portion 36 (the treatment instrument insertion hole portion 35a) so that the guide member 300 can move along the axial direction of the guide member 300. The second state shows that the rotary holding portion 530 fixes, together with the fixed holding portions 510, the proximal end portion 301 of the guide member 300 so that the guide member 300 is fixed and the displacement of the guide member 300 is prevented. In other words, the rotary holding portion 530 switches the holding state of the guide member 300 by rotation to either the first state in which the rotary holding portion 530 holds, together with the fixed holding portions 510, a part of the proximal end side of the guide member 300 exposed from the endoscope 10 at the operation portion 30, or the second state in which the rotary holding portion 530 fixes, together with the fixed holding portions 510, the part of the proximal end side of the guide member 300 exposed from the endoscope 10. The switch described above is performed while the distal end portion of the guide member 300 is protruding from the distal end opening portion 35c.

[First State]

As shown in FIG. 2A, FIG. 2B, and FIG. 3A, in the first state, the rotary-side insertion portion 531 communicates with the fixed-side insertion portions 511, and the whole portion rotary-side insertion portion 531 is provided in alignment with the whole portion fixed-side insertion portion 511. Moreover, in the first state, the guide member 300 which is inserted through the rotary-side insertion portion 531 and the fixed-side insertion portions 511 can move in the rotary-side insertion portion 531 and the fixed-side insertion portions 511 along the axial direction of the guide member 300 as a result of the aforementioned communication. In the first state, the guide member 300 slides on the rotary-side insertion portion 531 and the fixed-side insertion portions 511 along the axial direction of the guide member 300 when the guide member 300 moves. The central axis of the rotary-side insertion portion 531 is provided coaxially with the central axes of the fixed-side insertion portions 511.

[Second State]

As shown in FIG. 2C and FIG. 3B, in the second state, the rotary holding portion 530 is more shifted relative to the fixed holding portions 510 around the central axis of the body portion 31 than in the first state, and the rotary holding portion 530 fixes, together with the fixed holding portions 510, the guide member 300 by the shift of the rotary holding portion 530 relative to the fixed holding portions 510. Thus, the rotary holding portion 530 and the fixed holding portions 510 apply a shear force to the guide member 300 in a direction that intersects at right angles with the axial direction of the guide member 300. In this case, as shown in FIG. 2C, a force A1 applied to the guide member 300 by the rotary holding portion 530 is in a direction opposite to a force B1 applied to the guide member 300 by the fixed holding portions 510. The magnitude of the force A1 is substantially the same as the force B1. The force A1 and the force B1 are applied to the guide member 300 along the direction that intersects at right angles with the central axial direction of the guide member. The force A1 and the force B1 are substantially aligned in this orthogonal direction.

Specifically, as shown in FIG. 2C and FIG. 3B, the second state shows that the rotary-side insertion portion 531 is more shifted relative to the fixed-side insertion portions 511 in a direction around the central axis of the body portion 31 than in the first state. Thus, the second state shows that only a part of the rotary-side insertion portion 531 is provided in alignment with only parts of the fixed-side insertion portions 511, that only a part of the rotary-side insertion portion 531 communicates with only parts of the fixed-side insertion portions 511, and that the other part of the rotary-side insertion portion 531 is offset relative to and does no communicate with the other parts of the fixed-side insertion portions 511. That is, the second state shows that the central axis of the rotary-side insertion portion 531 is shifted relative to the central axes of the fixed-side insertion portions 511 in the direction around the central axis of the body portion 31. Further, the second state shows that the rotary-side insertion portion 531 is more shifted relative to the fixed-side insertion portions 511 in the direction around the central axis of the body portion 31, for example, substantially by a radius of the guide member 300 than in the first state.

As shown in FIG. 2C, in the second state, parts 531a and parts 511a press an outer circumferential surface of the guide member 300 in the communication parts between the rotary-side insertion portion 531 and the fixed-side insertion portions 511. In this instance, the parts 531a on the edge portion portions of the rotary-side insertion portion 531 and the parts 511a on the edge portion portions of the fixed-side insertion portions 511 apply the shear force to the guide member 300. In other words, the parts 531a and the parts 511a sandwich the guide member 300 therebetween. In the above, a force A2 applied to the guide member 300 by the parts 531a is in a direction opposite to a force B2 applied to the guide member 300 by the parts 511a. The magnitude of the force A2 is substantially the same as the force B2. The force A2 and the force B2 are applied to the guide member 300 along the direction that intersects at right angles with the central axial direction of the guide member. The force A2 and the force B2 are substantially aligned in this orthogonal direction. The force A2 corresponds to the force A1, and the force B2 corresponds to the force B1.

As shown in FIG. 2C, in the second state, the parts 531a on the edge portions of the rotary-side insertion portion 531 and the parts 511a on the edge portions of the fixed-side insertion portions 511 fix the movement of the guide member 300 along the axial direction of the guide member 300 by the pressing. When the parts 531a and the parts 511a press the outer circumferential surface of the guide member 300, the parts 531a and the parts 511a may cut into the outer circumferential surface of the guide member 300.

As shown in FIG. 2C, fixing which occurs by the aforementioned shear force and pressing is performed at two different places, that is, one end portion of the rotary-side insertion portion 531 and one fixed-side insertion portion 511, and the other end portion of the rotary-side insertion portion 531 and the other fixed-side insertion portion 511. That is, the guide member 300 is fixed at two different places such as one end portion of the rotary-side insertion portion 531 and one fixed-side insertion portion 511, and the other end portion of the rotary-side insertion portion 531 and the other fixed-side insertion portion 511. The fixing at the two places takes place at the same time when the rotary holding portion 530 is more shifted relative to the fixed holding portions 510 around the central axis of the body portion 31 than in the first state. That is, in the second state, the rotary-side insertion portion 531 is more shifted relative to the fixed-side insertion portions 511 in the direction around the central axis C of the operation portion 30 than in the first state at two places and at the same time. These two places exist coaxially in the central axis direction of the body portion 31.

Further, the second state shows that the guide member 300 which is inserted through the rotary-side insertion portion 531 and the fixed-side insertion portions 511 is fixed by the aforementioned shift. Moreover, in the second state, the guide member 300 is prevented from, for example, moving in the axial direction of the guide member 300, and is fixed.

[Positioning Mechanism 550]

As shown in FIG. 3A and FIG. 3B, the holding mechanism 500 further has a positioning mechanism 550 which positions the rotational position of the rotary holding portion 530 in either the first state or the second state.

As shown in FIG. 3A and FIG. 3B, the positioning mechanism 550 has a fixed-side positioning portion 551 which is provided in a part fixed to the rotary holding portion 530 that rotates, and a rotary-side positioning portion 553 which is provided in the rotary holding portion 530 that rotates and which freely engages with the fixed-side positioning portion 551. The fixed-side positioning portion 551 is provided at positions corresponding to the first state and the second state. The fixed-side positioning portion 551 is provided, for example, on the outer circumferential surface of the body portion 31 which is the part fixed to the rotary holding portion 530 that rotates. Thus, the rotary-side positioning portion 553 is provided, for example, on an inner circumferential surface of the rotary holding portion 530.

The fixed-side positioning portion 551 provided at the position corresponding to the first state is referred to as a fixed-side positioning portion 551a, and the fixed-side positioning portion 551 provided at the position corresponding to the second state is referred to as a fixed-side positioning portion 551b. The fixed-side positioning portion 551a is provided so that fixed-side positioning portion 551a is adjacent to the fixed-side positioning portion 551b in the direction around the central axis of the body portion 31. Specifically, the fixed-side positioning portion 551a is provided apart from the fixed-side positioning portion 551b in the direction around the central axis of the body portion 31 by the rotation amount of the rotary holding portion 530 to switch to the first state and the second state. This rotation amount represents, for example, substantially half of the radius of the guide member 300.

As shown in FIG. 3A and FIG. 3B, one of the fixed-side positioning portion 551 and the rotary-side positioning portion 553 has a projection portion, and the other has a depression portion which detachably engages with the projection portion.

As shown in FIG. 3A, when the rotary holding portion 530 rotates around the central axis of the body portion 31, the rotary-side positioning portion 553 engages with the fixed-side positioning portion 551a, thereby the rotary holding portion 530 is positioned in the first state.

As shown in FIG. 3B, when the rotary holding portion 530 rotates around the central axis of the body portion 31, the rotary-side positioning portion 553 engages with the fixed-side positioning portion 551b, thereby the rotary holding portion 530 is positioned in the second state.

[Functions]

For example, when a subject such as a bile duct 101 is treated with the treatment instrument 400, for example, an EST knife, the insertion portion 20 is inserted into a duodenum 100 as shown in FIG. 4A. A contrast tube 600 is then inserted into the bile duct 101 from the forceps plug portion 36 via the treatment instrument insertion hole portion 35*a*, the treatment instrument insertion channel, the treatment instrument raising base 51, and the distal end opening portion 35*c*. A contrast agent is then injected into the bile duct 101 via the contrast tube 600.

The guide member 300 is then inserted into the treatment instrument insertion channel from the forceps plug portion 36 via the treatment instrument insertion hole portion 35*a*. As shown in FIG. 4B, the distal end portion of the guide member 300 is inserted through the treatment instrument insertion channel, and protrudes from the distal end opening portion 35*c*. The distal end opening portion 35*c* is provided on the lateral side, thereby the distal end portion of the guide member 300 protrudes to the lateral side of the distal end portion of the insertion portion 20. The distal end portion of the guide member 300 then reaches a subject such as the bile duct 101. As shown in FIG. 2A, the proximal end portion 301 of the guide member 300 is exposed to the outside of the endoscope 10 from the forceps plug portion 36. The contrast tube 600 is then pulled out.

In the above, the guide member 300 is inserted by the right-hand operation of the surgeon while the grasping portion 33 is grasped with the left hand of the surgeon. The contrast tube 600 is pulled out by the right-hand operation of the surgeon while the grasping portion 33 is grasped with the left hand of the surgeon.

As shown in FIG. 4C and FIG. 4D, the treatment instrument 400 moves along the guide member 300 so that the guide member 300 passes through the cylindrical member 401 which functions as the monorail portion. In this instance, the treatment instrument 400 is guided by the guide member 300, and thus inserted into the treatment instrument insertion channel from the forceps plug portion 36 via the treatment instrument insertion hole portion 35*a*. The treatment instrument 400 is then guided by the guide member 300, and thus inserted through the treatment instrument insertion channel, protrudes to the lateral side from the distal end opening portion 35*c*, and reaches the subject.

Thus, the treatment instrument 400 is guided to the subject by the guide member 300.

In the above, the treatment instrument 400 is inserted by the right-hand operation of the surgeon while the grasping portion 33 is grasped with the left hand of the surgeon.

Although not shown, the proximal end portion of the treatment instrument 400 is exposed to the outside of the endoscope 10 from the forceps plug portion 36 in a manner similar to the proximal end portion 301 of the guide member 300.

As shown in FIG. 2A, FIG. 2B, and FIG. 3A, the rotary holding portion 530 then rotates around the central axis of the body portion 31, and the rotary-side positioning portion 553 engages with the fixed-side positioning portion 551*a*. Thus, the rotary holding portion 530 is positioned in the first state. The rotary-side insertion portion 531 is inserted through the fixed-side insertion portions 511. The proximal end portion 301 of the guide member 300 is then inserted through the rotary-side insertion portion 531 and the fixed-side insertion portions 511. This insertion prevents the proximal end portion 301 of the guide member 300 from coming off the fixed holding portions 510 and the rotary holding portion 530. The holding mechanism 500 then holds the proximal end portion 301 of the guide member 300. Thus, the proximal end portion 301 of the guide member 300 is attached to the operation portion 30. The proximal end portion 301 of the guide member 300 is inserted through the rotary-side insertion portion 531 and the fixed-side insertion portions 511 by the right-hand operation of the surgeon while the grasping portion 33 is grasped with the left hand of the surgeon. The proximal end portion 301 is movable relative to the holding mechanism 500 along the axial direction of the guide member 300.

As shown in FIG. 2C and FIG. 3B, the rotary holding portion 530 rotates around the central axis of the body portion 31, and the rotary-side positioning portion 553 engages with the fixed-side positioning portion 551*b*. As a result, the rotary holding portion 530 is positioned in the second state. In this instance, the rotary holding portion 530 is more shifted relative to the fixed holding portions 510 around the central axis of the body portion 31 than in the first state, the rotary holding portion 530 and the fixed holding portions 510 apply the shear force to the guide member 300 by the shift in the direction that intersects at right angles with the axial direction of the guide member 300, and the rotary holding portion 530 fixes, together with the fixed holding portions 510, the guide member 300 by the shift and the shear force. Specifically, in the communication parts between the rotary-side insertion portion 531 and the fixed-side insertion portions 511, the parts 531*a* on the edge portions of the rotary-side insertion portion 531 and the parts 511*a* on the edge portions of the fixed-side insertion portions 511 apply the shear force to the guide member 300, and the parts 531*a* and the parts 511*a* press the outer circumferential surface of the guide member 300. As a result of this pressing, the parts 531*a* and the parts 511*a* fix the guide member 300. The fixing is performed at two different places, that is, one end portion of the rotary-side insertion portion 531 and one fixed-side insertion portion 511, and the other end portion of the rotary-side insertion portion 531 and the other fixed-side insertion portion 511. The fixing at the two places is performed at the same time when the rotary holding portion 530 is more shifted relative to the fixed holding portions 510 around the central axis of the body portion 31 than in the first state.

Thus, the proximal end portion 301 of the guide member 300 is prevented from moving, for example, in the axial direction of the guide member 300, is fixed, and is prevented from being displaced. The proximal end portion 301 of the guide member 300 is then fixedly attached to the operation portion 30. Thus, the holding mechanism 500 keeps the proximal end portion 301 of the guide member 300 fixed.

When the parts 531*a* on the edge portions of the rotary-side insertion portion 531 and the parts 511*a* on the edge portions of the fixed-side insertion portions 511 press the outer circumferential surface of the guide member 300, a reaction force of the guide member 300 urges the rotary holding portion 530 to return to the first state from the second state. However, since the rotary-side positioning portion 553 engages with the fixed-side positioning portion 551*b*, the rotary holding portion 530 is surely positioned and fixed in the second state, and the proximal end portion 301 of the guide member 300 is prevented from moving, for example, in the axial direction of the guide member 300, is fixed, and is prevented from being displaced.

The rotary holding portion 530 is rotated by the right-hand operation of the surgeon while the grasping portion 33 is grasped with the left hand of the surgeon.

In this state, the treatment instrument 400 then treats the subject. After the finish of the treatment by the treatment instrument 400, the treatment instrument 400 is pulled out of the endoscope 10 while the guide member 300 remains in the vicinity of the subject.

In this instance, as shown in FIG. 2C and FIG. 3B, the holding mechanism 500 fixes the proximal end portion 301 of the guide member 300 as described above. As a result, the guide member 300 is fixed to the operation portion 30, and the displacement of the guide member 300 that may be caused by the pull-out of the treatment instrument 400 is prevented.

If the cylindrical member 401 which functions as the monorail portion and which is thicker than the treatment instrument 400 is pulled out of the forceps plug portion 36 and reaches the holding mechanism 500, the rotary holding portion 530 rotates around the central axis of the body portion 31, and the rotary-side positioning portion 553 engages with the fixed-side positioning portion 551a. As a result, the rotary holding portion 530 is positioned in the first state. The guide member 300 is pulled out of the fixed holding portions 510 and the rotary holding portion 530, and the cylindrical member 401 is pulled out of the guide member 300. The treatment instrument 400 is then pulled out of the endoscope 10, and also detached from the guide member 300. In the above, the treatment instrument 400 is detached by the right-hand operation of the surgeon while the grasping portion 33 is grasped with the left hand of the surgeon. The guide member 300 remains in the endoscope 10 and in the body.

An unshown basket is then guided by the guide member 300 in a manner similar to the treatment instrument 400, and then inserted into the treatment instrument insertion channel from the forceps plug portion 36 via the treatment instrument insertion hole portion 35a. The basket is then guided by the guide member 300, and thus inserted through the treatment instrument insertion channel, protrudes to the lateral side from the distal end opening portion 35c, and reaches the subject. The holding mechanism 500 then fixedly holds the proximal end portion 301 of the guide member 300 again as described above. The basket then collects, for example, a gallstone. The basket is pulled out of the endoscope 10.

When the basket is removed from the forceps plug portion 36 and discharged to the outside of the endoscope 10, the rotary holding portion 530 rotates around the central axis of the body portion 31, and the rotary-side positioning portion 553 engages with the fixed-side positioning portion 551a, in a manner similar to the above. As a result, the rotary holding portion 530 is positioned in the first state. The guide member 300 is pulled out of the fixed holding portions 510 and the rotary holding portion 530, and the basket is also detached from the guide member 300. The guide member 300 is then pulled out of the endoscope 10.

[Advantageous Effects]

According to the present embodiment, in the first state shown in FIG. 2A, FIG. 2B, and FIG. 3A, the proximal end portion 301 of the guide member 300 is inserted through the rotary-side insertion portion 531 and the fixed-side insertion portions 511, thereby the holding mechanism 500 holds the proximal end portion 301 of the guide member 300. The rotary holding portion 530 rotates as shown in FIG. 2C and FIG. 3B so that the state is switched from the first state to the second state, and the holding mechanism 500 fixes the proximal end portion 301 of the guide member 300. Thus, according to the present embodiment, it is possible to simplify the work of holding and fixing the guide member 300, and prevent the shift of the guide member 300.

According to the present embodiment, it is possible to rotate the rotary holding portion 530 with the right hand while grasping the grasping portion 33 with the left hand, and adjust the position of the guide member 300 with the right hand in the first state.

According to the present embodiment, in the second state shown in FIG. 2C and FIG. 3B, the rotary holding portion 530 is more shifted relative to the fixed holding portions 510 around the central axis of the body portion 31 than in the first state, the rotary holding portion 530 and the fixed holding portions 510 apply the shear force to the guide member 300 in the direction that intersects at right angles with the axial direction of the guide member 300 by the shift, and the rotary holding portion 530 fixes, together with the fixed holding portions 510, the guide member 300 by the shift and the shear force. Thus, according to the present embodiment, it is possible to fix the guide member 300 and prevent the shift of the guide member 300 by the simple work such as rotating the rotary holding portion 530.

According to the present embodiment, as shown in FIG. 2A and FIG. 2B, the fixed holding portions 510 can hold the guide member 300 by the fixed-side insertion portions 511, and the rotary holding portion 530 can hold the guide member 300 by the rotary-side insertion portion 531.

According to the present embodiment, in the second state shown in FIG. 2C and FIG. 3B, the rotary-side insertion portion 531 is more shifted relative to the fixed-side insertion portions 511 in the direction around the central axis of the body portion 31 than in the first state. In the communication parts between the rotary-side insertion portion 531 and the fixed-side insertion portions 511, the parts 531a on the edge portions of the rotary-side insertion portion 531 and the parts 511a on the edge portions of the fixed-side insertion portions 511 apply the shear force to the guide member 300, and the parts 531a and the parts 511a press the outer circumferential surface of the guide member 300. As a result of the pressing, the parts 531a and the parts 511a fix the guide member 300. Thus, according to the present embodiment, it is possible to surely fix the guide member 300, and surely prevent the displacement of the guide member 300.

According to the present embodiment, as shown in FIG. 2A, FIG. 2B, and FIG. 2C, a pair of fixed holding portions 510 are provided so that the fixed holding portions 510 sandwich the rotary holding portion 530 therebetween in the direction of the central axis C of the operation portion 30. Thus, according to the present embodiment, it is possible to easily position the rotary holding portion 530. According to the present embodiment, in the second state shown in FIG. 2C, the fixing can perform at different two places, that is, one end portion of the rotary-side insertion portion 531 and one fixed-side insertion portion 511, and the other end portion of the rotary-side insertion portion 531 and the other fixed-side insertion portion 511. Thus, according to the present embodiment, it is possible to prevent the guide member 300 from moving, for example, in the axial direction of the guide member 300, and surely fix the guide member 300. According to the present embodiment, the fixing at the two places can perform at the same time when the rotary holding portion 530 is more shifted relative to the fixed holding portions 510 around the central axis C of the operation portion 30 than in the first state.

According to the present embodiment, as described above, fixing performs at different two places: one end portion of the rotary-side insertion portion 531 and one fixed-side insertion portion 511, and the other end portion of the rotary-side insertion portion 531 and the other fixed-side insertion portion 511. According to the present embodiment, the fixing at the two places performs at the same time when the rotary holding portion 530 is more shifted relative to the fixed holding portions 510 around the central axis C of the operation portion 30 than in the first state. Thus, according to the present embodiment, it is possible to carry out the above by one easy work such as rotating the rotary holding portion 530.

According to the present embodiment, the rotary holding portion 530 can be surely positioned in either the first state or the second state by the positioning mechanism 550 shown in FIG. 3A and FIG. 3B. In particular, the reaction force of the guide member 300 urges the rotary holding portion 530 to return to the first state from the second state. However, the rotary-side positioning portion 553 engages with the fixed-side positioning portion 551b, so that according to the present embodiment, it is possible to surely position and fix the rotary holding portion 530 in the second state. Therefore, according to the present embodiment, it is possible to prevent the proximal end portion 301 of the guide member 300 from moving, for example, in the axial direction of the guide member 300, fix the proximal end portion 301 of the guide member 300, and prevent the displacement of the proximal end portion 301 of the guide member 300.

According to the present embodiment, as shown in FIG. 2B, it is possible to prevent the guide member 300 from coming off the fixed holding portions 510 by the fixed-side insertion portions 511, and prevent the guide member 300 from coming off the rotary holding portion 530 by the rotary-side insertion portion 531.

According to the present embodiment, as shown in FIG. 2A, FIG. 2B, and FIG. 2C, the rotary holding portion 530 has a circular cylindrical shape, and is provided around the circumference of the body portion 31. The central axis of the rotary holding portion 530 is provided, for example, on the central axis of the body portion 31. Thus, according to the present embodiment, it is possible to improve the operability of the rotary holding portion 530.

For example, when a general holding mechanism different from the holding mechanism 500 according to the present embodiment is incorporated in the distal end hard portion 21 in the vicinity of the distal end opening portion 35c, the distal end hard portion 21 is thicker. In this case, the holding state of the general holding mechanism cannot be visually recognized.

Suppose that a holding portion of the general holding mechanism functions as a groove portion provided in the treatment instrument raising base 51. When a diameter of one guide member 300 is different from a diameter of the other guide member 300 for replacement, the holding portion might not be able to surely hold both the guide members. When the distal end portion of the guide member 300 has a tapered shape, the holding portion might not be able to surely hold the guide member 300.

Suppose that the holding portion functions as a groove portion provided in the treatment instrument raising base 51. When the treatment instrument 400 is pulled out while the guide member 300 is remaining, the cylindrical member 401 which functions as the monorail portion needs to pass through the holding portion which functions as the groove portion. In this case, the holding portion needs to release a guide wire, but the guide member 300 might be shifted due to the release.

However, according to the present embodiment, it is possible to solve the above problem.

According to the present embodiment, it is possible to clean the holding mechanism 500 together with the endoscope 10 because the holding mechanism 500 is exposed to the outside. According to the present embodiment, the fixed holding portions 510 and the rotary holding portion 530 are detachable to increase cleaning efficiency. At least one of the fixed holding portions 510 and the rotary holding portion 530 may be detachably fixed to the operation portion 30.

[Other]

According to the present embodiment, the rotary holding portion 530 may be rotatable, for example, around the central axis of the body portion 31.

The fixed holding portions 510 have the fixed-side insertion portions 511, but do not need to be limited to this. The fixed holding portions 510 may have unshown groove portions. The groove portions are recessed toward the inner circumferential surfaces of the fixed holding portions 510 from the outer circumferential surfaces of the fixed holding portions 510. The groove portions are provided along the central axis direction of the fixed holding portions 510. Each of the groove portions has a coming-off prevention portion which functions as an unshown projection-depression portion provided in an inner circumferential surface of the groove portion or as an unshown claw portion which hold the guide member 300 and prevent the guide member 300 from coming off the groove portion. The inner circumferential surfaces of the groove portions may have a corrugated shape to prevent coming off. The inner circumferential surfaces of the groove portions may be coated to prevent coming off.

The same also applies to the rotary holding portion 530.

As shown in FIG. 5, the rotary holding portion 530 and the fixed holding portions 510 may be provided so that the fixed-side insertion portions 511 and the rotary-side insertion portion 531 are provided at positions different from the forceps plug portion 36 in the direction around the central axis of the body portion 31, for example, provided on a side surface of the body portion 31.

The fixed holding portions 510 are detachably fixed to, for example, the outer circumferential surface of the body portion 31. How to attach and detach the fixed holding portions 510 is not particularly limited.

Figure 6B:
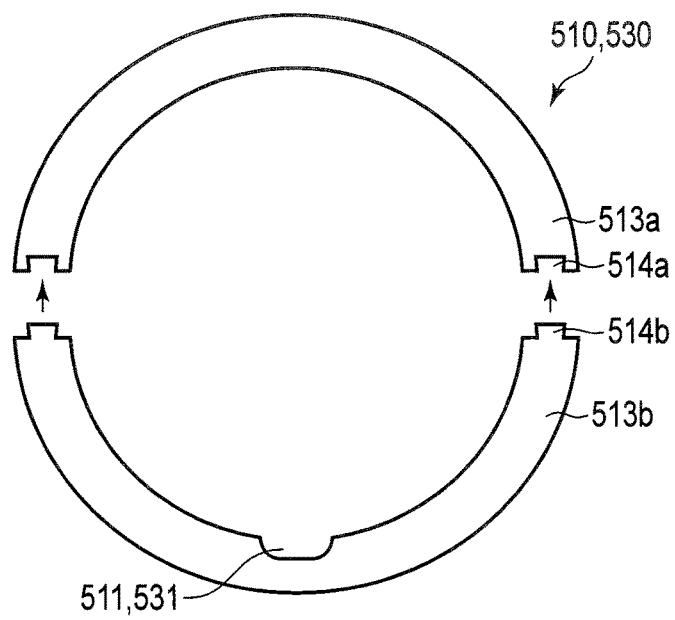
FIG. 6B is a diagram showing an example of the attachment and detachment of the fixed holding portion and the rotary holding portion, and showing the separation type.

As shown in FIG. 6A and FIG. 6B, for example, the circular cylindrical fixed holding portion 510 may be separable into two U-shaped holding members 513a and 513b. One holding member 513a has depression portions 514a provided at both end portions of the U-shape. The other holding member 513b has projection portions 514b which are provided at both end portions of the U-shape and which engage with the depression portions 514a. For example, the depression portions 514a have a rounded shape shown in FIG. 6A or a rectangular shape shown in FIG. 6B. The depression portions 514a are not particularly limited in shape. For example, the projection portions 514b have a rounded shape shown in FIG. 6A or a rectangular shape shown in FIG. 6B. The projection portions 514b are not particularly limited in shape.

Figure 7A:
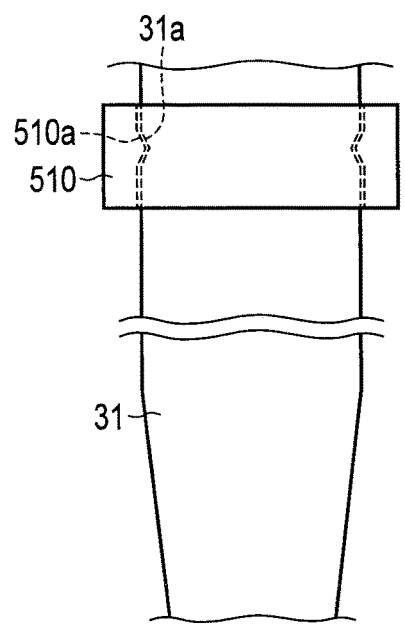
FIG. 7A is a diagram showing an example of the attachment and detachment of the fixed holding portion and the rotary holding portion, and showing a slide type.
Figure 7B:
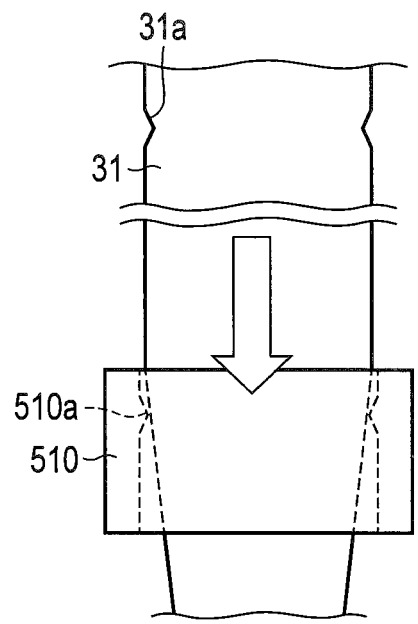
FIG. 7B is a diagram showing an example of the attachment and detachment of the fixed-side holding portion and the rotary-side holding portion, and showing the slide type.

As shown in FIG. 7A and FIG. 7B, for example, the fixed holding portion 510 may be attached to the body portion 31 by the sliding of the insertion portion 20 and the body portion 31 in the central axis direction of the insertion portion 20. In this case, the fixed holding portion 510 may have a projection portion 510a which detachably engages with a depression portion 31a provided in the outer circumferential surface of the body portion 31 and which is provided on the inner circumferential surface of the fixed holding portion 510. The depression portion 31a is provided, for example, around the circumference of the body portion 31. The projection portion 510a is provided, for example, around the circumference of the fixed holding portion 510.

As a result, the fixed holding portion 510 is easily positioned in the central axis direction of the body portion 31.

The contents in FIG. 6A, FIG. 6B, FIG. 7A, and FIG. 7B described above also apply to the rotary holding portion 530.

In the above, although not shown, one fixed holding portion 510 provided on the side of the operation portion 30 may be integrally fixed to the body portion 31, and the other fixed holding portion 510 provided on the side of the insertion portion 20 may be detachably fixed to the outer circumferential surface of the body portion 31 as described above.

In the above, the fixed holding portions 510 may be integrally fixed to the body portion 31, and the rotary holding portion 530 may be attachable to and detachable from the body portion 31. In this case, as shown in FIG. 6A and FIG. 6B, the rotary holding portion 530 alone is separable into, for example, two U-shaped holding members.

Figure 8A:
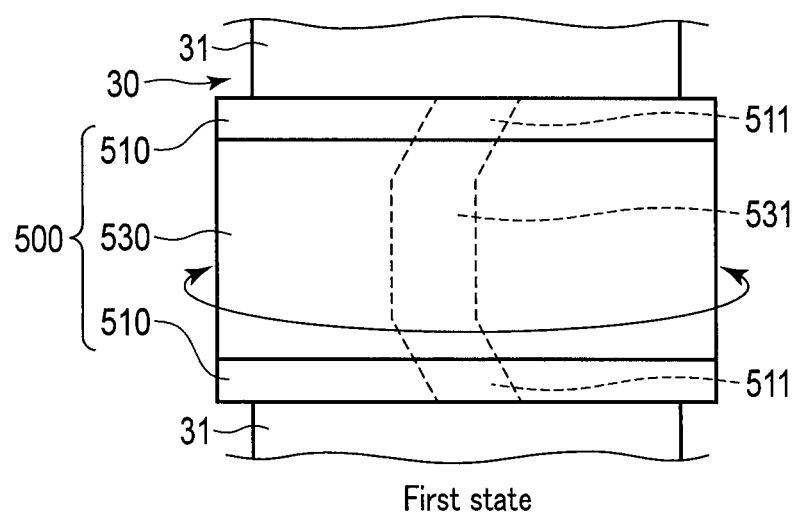
FIG. 8A is a diagram showing an example of the fixed-side insertion portion and the rotary-side insertion portion, and showing the first state.

The fixed-side insertion portions 511 and the rotary-side insertion portion 531 are linearly provided, but do not need to be limited to this. As shown in FIG. 8A and FIG. 8B, for example, the fixed-side insertion portions 511 may linearly skew relative to the central axis direction of the fixed holding portions 510, and the rotary-side insertion portion 531 may be substantially U-shaped. This can prevent the guide member 300 from coming off the fixed-side insertion portions 511 and the rotary-side insertion portion 531 even in the first state shown in FIG. 8A.

Figure 9C:
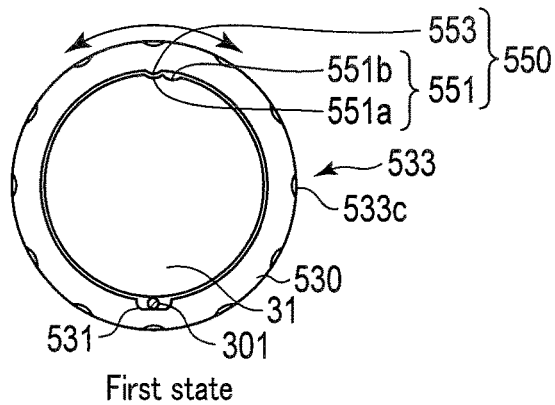
FIG. 9C is a diagram showing an example of the operation portion which operates the rotary holding portion.

As shown in FIG. 9A, FIG. 9B, and FIG. 9C, the rotary holding portion 530 may have an operation portion 533 which is provided on the outer circumferential surface of the rotary holding portion 530 and which operates the rotation of the rotary holding portion 530. The operation portion 533 has at least one of a knob portion 533a which functions as a projecting portion projecting from the outer circumferential surface of the rotary holding portion 530 as shown in FIG. 9A, a cutout portion 533b which is formed by cutting out part of the outer circumferential surface of the rotary holding portion 530 as shown in FIG. 9B, and a depression portion 533c which is provided in the outer circumferential surface of the rotary holding portion 530 as shown in FIG. 9C.

Figure 10A:
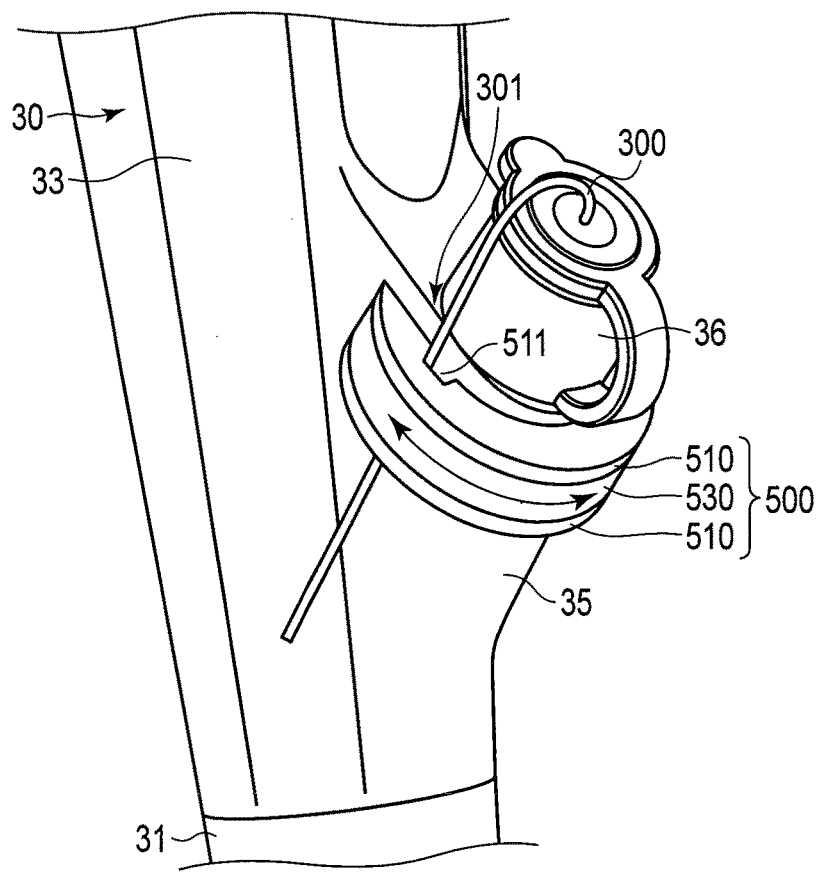
FIG. 10A is a perspective view showing an example of the arrangement position of the holding mechanism, and showing the part around the holding mechanism which is provided in a treatment instrument insertion portion.

As shown in FIG. 10A, the fixed holding portions 510 and the rotary holding portion 530 may be provided in the treatment instrument insertion portion 35.

In this case, the fixed holding portions 510 are fitted into the treatment instrument insertion portion 35 from a lateral side of the treatment instrument insertion portion 35 to be fixed to the treatment instrument insertion portion 35. The fixed holding portions 510 are attachable to and detachable from the outer circumferential surface of the treatment instrument insertion portion 35. Thus, the fixed holding portions 510 are, for example, C-shaped.

The rotary holding portion 530 is fitted into the treatment instrument insertion portion 35 from the lateral side of the treatment instrument insertion portion 35 to be provided in the treatment instrument insertion portion 35. The rotary holding portion 530 is attachable to and detachable from the outer circumferential surface of the treatment instrument insertion portion 35. Thus, the rotary holding portion 530 is, for example, C-shaped. The length of circumferential surface of the rotary holding portion 530 is shorter than the length of circumferential surface of each of the fixed holding portions 510 so that the rotary holding portion 530 rotates around the central axis of the treatment instrument insertion portion 35.

In this case, the holding mechanism 500 can hold the proximal end portion 301 of the guide member 300 immediately pulled out of the forceps plug portion 36. Therefore, it is possible to accurately prevent the displacement of the guide member 300.

As shown in FIG. 10B, the fixed holding portions 510 and the rotary holding portion 530 may be provided higher than the treatment instrument insertion portion 35, for example, provided in the grasping portion 33.

In this case, the fixed holding portions 510 are fitted into the grasping portion 33 from a lateral side of the grasping portion 33 to be fixed to the grasping portion 33. The fixed holding portions 510 are attachable to and detachable from the outer circumferential surface of the grasping portion 33. Thus, the fixed holding portions 510 are, for example, C-shaped.

The rotary holding portion 530 is fitted into the grasping portion 33 from the lateral side of the grasping portion 33 to be provided in the grasping portion 33. The rotary holding portion 530 is attachable to and detachable from the outer circumferential surface of the grasping portion 33. Thus, the rotary holding portion 530 is, for example, C-shaped. The length of circumferential surface of the rotary holding portion 530 is shorter than the length of circumferential surface of the fixed holding portion 510 so that the rotary holding portion 530 rotates around the central axis of the grasping portion 33.

In this case, the rotary holding portion 530 can be rotated by the fingers of the left hand grasping the grasping portion 33.

The positioning mechanism 550 has the fixed-side positioning portion 551 provided on the outer circumferential surface of the operation portion 30, and the rotary-side positioning portion 553 which is provided on the inner circumferential surface of the rotary holding portion 530 and which freely engages with the fixed-side positioning portion 551, but does not need to be limited to this.

In the positioning mechanism 550, although not shown, the fixed-side positioning portion 551 may be provided, for example, in the end face of the fixed holding portion 510 which is, for example, a part fixed to the rotary holding portion 530 that rotates. This end face is, for example, ring-shaped. This end face contacts the ring-shaped end face of the rotary holding portion 530, and functions as a slide surface on which the end face of the rotary holding portion 530 slides when the rotary holding portion 530 rotates. Accordingly, the rotary-side positioning portion 553 is provided in the end face of the rotary holding portion 530.

According to the present embodiment, the endoscope 10 is a side-viewing type, but may be a forward-viewing type.

Second Embodiment

Below, only the differences between the first embodiment and the second embodiment are described, with reference to FIG. 11A, FIG. 11B, FIG. 11C, FIG. 11D, FIG. 11E, and FIG. 11F.

In the first embodiment, only one guide member 300 is used. According to the present embodiment, more than one guide member 300, for example, two guide members 300 are used, as shown in FIG. 11A. For convenience of explanation, one guide member 300 is referred to as a guide member 300a, and the other guide member 300 is referred to as a guide member 300b.

[Fixed Holding Portions 510]

The same number of fixed holding portions 510 as the guide members 300, for example, two fixed holding portions 510 are provided. For convenience of explanation, as shown in FIG. 11A, one fixed holding portion 510 is referred to as a fixed holding portion 515, and the other fixed holding portion 510 is referred to as a fixed holding portion 517.

In one fixed holding portion 510, the same number of fixed-side insertion portions 511 as the guide members 300, for example, two fixed-side insertion portions 511 are provided. The fixed-side insertion portions 511 are provided apart from each other in the direction around the central axis of one fixed holding portion 510. The fixed-side insertion portions 511 are separate from each other.

For convenience of explanation, as shown in FIG. 11A, the fixed holding portion 515 has fixed-side insertion portions 515a and 515b, and the fixed holding portion 517 has fixed-side insertion portions 517a and 517b.

[Rotary Holding Portions 530]

The same number of rotary holding portions 530 as the guide members 300, for example, two rotary holding portions 530 are provided. The rotary holding portions 530 are provided adjacent to each other along the central axis direction of the body portion 31. The rotary holding portions 530 rotate so that the holding state of the holding mechanism 500 which holds the guide members 300 switches to either the first state or the second state for each of the guide members 300.

For convenience of explanation, as shown in FIG. 11A, one rotary holding portion 530 is referred to as a rotary holding portion 535, and the other rotary holding portion 530 is referred to as a rotary holding portion 537.

In one rotary holding portion 530, the same number of rotary-side insertion portions 531 as the guide members 300, for example, two rotary-side insertion portions 531 are provided. The rotary-side insertion portions 531 are provided apart from each other in the direction around the central axis of the rotary holding portion 530. The rotary-side insertion portions 531 are separate from each other.

For convenience of explanation, as shown in FIG. 11A, the rotary holding portion 535 has rotary-side insertion portions 535a and 535b, and the rotary holding portion 537 has rotary-side insertion portions 537a and 537b.

Figure 11B:
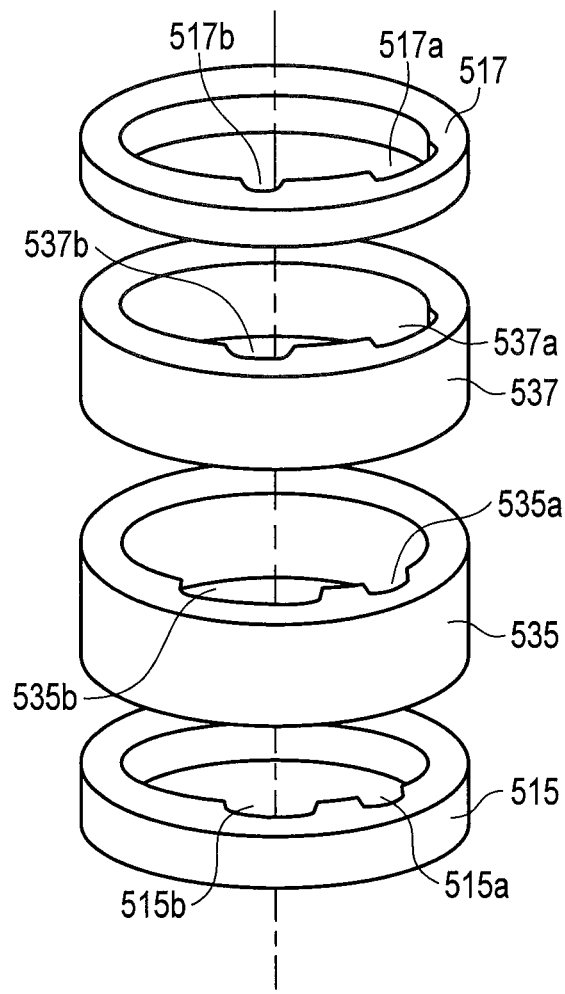
FIG. 11B is a diagram showing the positional relation between one fixed holding portion, the other fixed holding portion, one rotary holding portion, and the other rotary holding portion.

As shown in FIG. 11A and FIG. 11B, the rotary holding portions 535 and 537 are sandwiched between the fixed holding portions 515 and 513, for example, in the central axis direction of the body portion 31 as in the first embodiment. As has been described above, the fixed-side insertion portion is provided in each fixed holding portion, and the rotary-side insertion portion is provided in each rotary holding portion.

[Definitions for Convenience of Explanation]

The following are defined for convenience of explanation in addition to the above.

As shown in FIG. 11A, the fixed holding portion 515, the rotary holding portion 535, the rotary holding portion 537, and the fixed holding portion 517 are provided in order from the proximal end portion of the insertion portion 20 toward the operation portion 30.

The rotary holding portion 535 fixes the guide member 300a, and the rotary holding portion 537 fixes the guide member 300b.

The guide member 300a is inserted through the fixed-side insertion portion 515a, the rotary-side insertion portion 535a, the rotary-side insertion portion 537a, and the fixed-side insertion portion 517a.

The guide member 300b is inserted through the fixed-side insertion portion 515b, the rotary-side insertion portion 535b, the rotary-side insertion portion 537b, and the fixed-side insertion portion 517b.

Figure 11C:
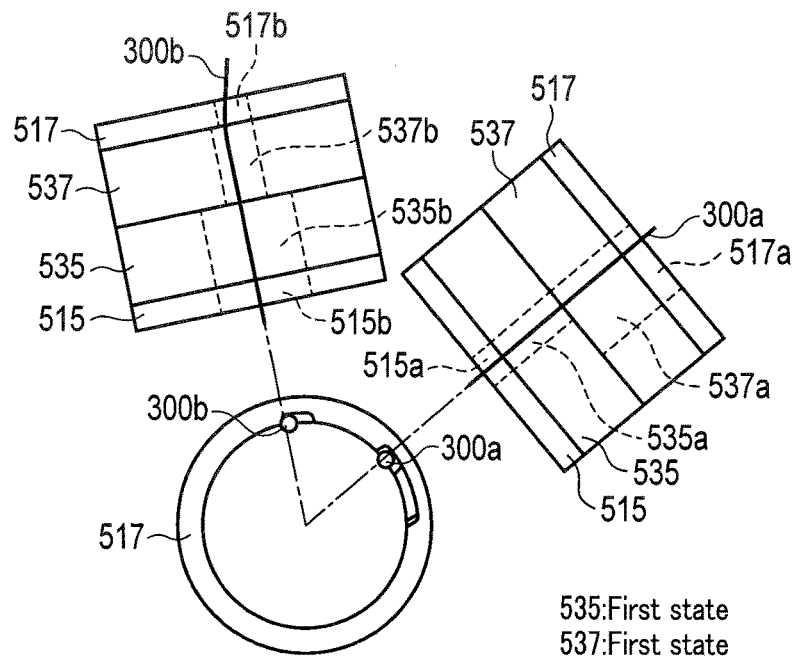
FIG. 11C is a diagram illustrating that both of the rotary holding portions are in the first state.

[FIG. 11C•Rotary Holding Portion 535 and Rotary Holding Portion 537 are in First State]

As shown in FIG. 11C, in the first state, the rotary-side insertion portion 537a communicates with the fixed-side insertion portion 517a, the rotary-side insertion portion 535a communicates with the rotary-side insertion portion 537a, and the rotary-side insertion portion 535a communicates with the fixed-side insertion portion 515a in the axial direction of the body portion 31 so that the guide member 300a is inserted through the fixed-side insertion portion 517a, the rotary-side insertion portion 537a, the rotary-side insertion portion 535a, and the fixed-side insertion portion 515a in order.

As shown in FIG. 11C, in the first state, the rotary-side insertion portion 537b communicates with the fixed-side insertion portion 517b, the rotary-side insertion portion 535b communicates with the rotary-side insertion portion 537b, and the rotary-side insertion portion 535b communicates with the fixed-side insertion portion 515b in the axial direction of the body portion 31 so that the guide member 300b is inserted through the fixed-side insertion portion 517b, the rotary-side insertion portion 537b, the rotary-side insertion portion 535b, and the fixed-side insertion portion 515b in order.

[FIG. 11E•Rotary Holding Portion 535 is in Second State•Rotary Holding Portion 537 is in First State]

As shown in FIG. 11E, this state shows that the guide members 300a and 300b are held so that the guide member 300a is fixed and so that the guide member 300b is movable in the axial direction of the guide member 300. In this case, the rotary holding portion 535 alone rotates around the central axis of the body portion 31. That is, the rotary holding portion 535 moves relative to the fixed holding portion 515, the rotary holding portion 537, and the fixed holding portion 517.

In this case, the rotary holding portion 535 is more shifted relative to the fixed holding portion 515 around the central axis of the body portion 31 than in the first state shown in FIG. 11C, the rotary holding portion 535 and the fixed holding portion 515 apply the shear force to the guide member 300a in the direction that intersects at right angles with the axial direction of the guide member 300a by the shift, and the rotary holding portion 535 fixes, together with the fixed holding portion 515, the guide member 300a by the shift and the shear force.

In the second state, the rotary-side insertion portion 535a is more shifted relative to the fixed-side insertion portion 515a around the central axis of the body portion 31 than in the first state shown in FIG. 11C. The second state shows that a part 535a1 on the edge portion of the rotary-side insertion portion 535a and a part 515a1 on the edge portion of the fixed-side insertion portion 515a apply the shear force to the guide member 300a, and the part 535a1 and the part 515a1 press the outer circumferential surface of the guide member 300a in the communication part between the rotary-side insertion portion 535a and the fixed-side insertion portion 515a. The second state shows that the part 535a1 and the part 515a1 fix the guide member 300a by the pressing.

In this case, in the axial direction of the body portion 31, the rotary-side insertion portion 535a communicates with the rotary-side insertion portion 537a, and the rotary-side insertion portion 537a communicates with the fixed-side insertion portion 517a.

In this case, the rotary-side insertion portion 537b communicates with the fixed-side insertion portion 517b, the rotary-side insertion portion 535b communicates with the fixed-side insertion portion 515b, and the rotary-side insertion portion 535*b* communicates with the rotary-side insertion portion 537*b* in the axial direction of the body portion 31 so that the guide member 300*b* is movable.

Figure 11D:
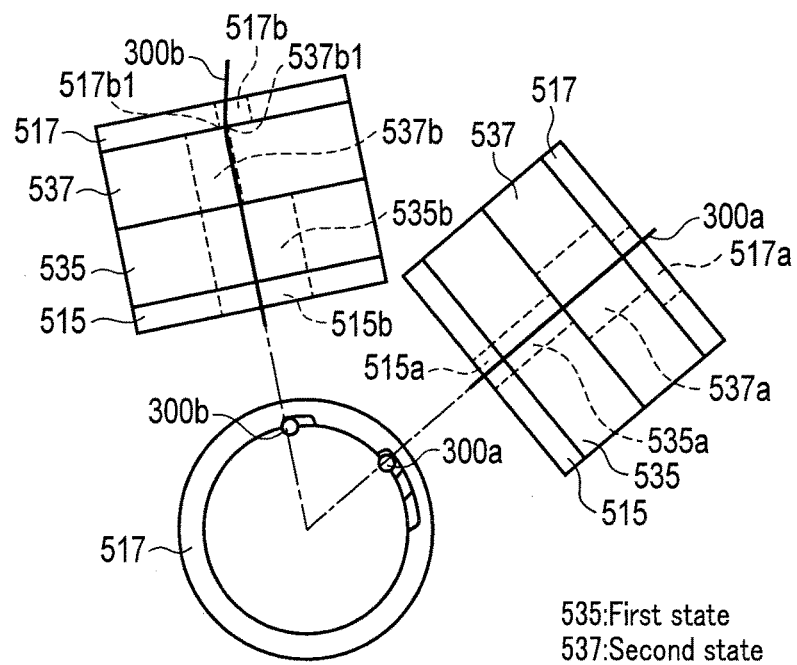
FIG. 11D is a diagram illustrating that one rotary holding portion is in the first state and that the other rotary holding portion is in the second state.

[FIG. 11D•Rotary Holding Portion 535 is in First State•Rotary Holding Portion 537 is in Second State]

As shown in FIG. 11D, this state shows that the guide members 300*a* and 300*b* are held so that the guide member 300*b* is fixed and so that the guide member 300*a* is movable in the axial direction of the guide member 300. In this case, the rotary holding portion 537 alone rotates around the central axis of the body portion 31. That is, the rotary holding portion 537 moves relative to the fixed holding portion 515, the rotary holding portion 535, and the fixed holding portion 517. The rotation direction of the rotary holding portion 537 is reversed to the direction in which the rotary holding portion 537 has rotated because the rotary holding portion 535 is in the second state in FIG. 11E.

In this case, the rotary holding portion 537 is more shifted relative to the fixed holding portion 517 around the central axis of the body portion 31 than in the first state shown in FIG. 11C, the rotary holding portion 537 and the fixed holding portion 517 apply the shear force to the guide member 300*b* in the direction that intersects at right angles with the axial direction of the guide member 300*b* by the shift, and the rotary holding portion 537 fixes, together with the fixed holding portion 517, the guide member 300*b* by the shift and the shear force.

In the second state, the rotary-side insertion portion 537*b* is more shifted relative to the fixed-side insertion portion 517*b* around the central axis of the body portion 31 than in the first state shown in FIG. 11C. The second state shows that a part 537*b*1 on the edge portion of the rotary-side insertion portion 537*b* and a part 517*b*1 on the edge portion of the fixed-side insertion portion 517*b* apply the shear force to the guide member 300*b*, and the part 537*b*1 and the part 517*b*1 press the outer circumferential surface of the guide member 300*b* in the communication part between the rotary-side insertion portion 537*b* and the fixed-side insertion portion 517*b*. The second state shows that the part 537*b*1 and the part 517*b*1 fix the guide member 300*b* by the pressing.

In this case, in the axial direction of the body portion 31, the rotary-side insertion portion 535*b* communicates with the fixed-side insertion portion 515*b*, and the rotary-side insertion portion 535*b* communicates with the rotary-side insertion portion 537*b*.

In this case, the rotary-side insertion portion 537*a* communicates with the fixed-side insertion portion 517*a*, the rotary-side insertion portion 535*a* communicates with the fixed-side insertion portion 515*a*, and the rotary-side insertion portion 535*a* communicates with the rotary-side insertion portion 537*a* so that the guide member 300*a* is movable in the axial direction of the body portion 31.

[FIG. 11F•Rotary Holding Portion 535 is in Second State•Rotary Holding Portion 537 is in Second State]

As shown in FIG. 11F, this state shows that the guide member 300*a* is fixed and that the guide member 300*b* is fixed. In this case, the rotary holding portions 535 and 537 rotate around the central axis of the body portion 31. A rotation direction of the rotary holding portion 535 is reversed to a rotation direction of the rotary holding portion 537.

This state is a combination of [Rotary Holding Portion 535 is in Second State] shown in FIG. 11E and [Rotary Holding Portion 537 is in Second State] shown in FIG. 11D.

In this case, the rotary holding portion 535 is more shifted relative to the fixed holding portion 515 around the central axis of the body portion 31 than in the first state shown in FIG. 11C, the rotary holding portion 535 and the fixed holding portion 515 apply the shear force to the guide member 300*a* in the direction that intersects at right angles with the axial direction of the guide member 300*a* by the shift, and the rotary holding portion 535 fixes, together with the fixed holding portion 515, the guide member 300*a* by the shift and the shear force.

In the second state, the rotary-side insertion portion 535*a* is more shifted relative to the fixed-side insertion portion 515*a* around the central axis of the body portion 31 than in the first state shown in FIG. 11C. The second state shows that the part 535*a*1 on the edge portion of the rotary-side insertion portion 535*a* and the part 515*a*1 on the edge portion of the fixed-side insertion portion 515*a* apply the shear force to the guide member 300*a*, and the part 535*a*1 and the part 515*a*1 press the outer circumferential surface of the guide member 300*a* in the communication part between the rotary-side insertion portion 535*a* and the fixed-side insertion portion 515*a*. The second state shows that the part 535*a*1 and the part 515*a*1 fix the guide member 300*a* by the pressing.

In this case, in the axial direction of the body portion 31, the rotary-side insertion portion 537*a* communicates with the rotary-side insertion portion 535*a*, and the rotary-side insertion portion 537*a* communicates with the fixed-side insertion portion 517*a*.

The rotary holding portion 537 is more shifted relative to the fixed holding portion 517 around the central axis of the body portion 31 than in the first state shown in FIG. 11C, the rotary holding portion 537 and the fixed holding portion 517 apply the shear force to the guide member 300*b* in the direction that intersects at right angles with the axial direction of the guide member 300*b* by the shift, and the rotary holding portion 537 fixes, together with the fixed holding portion 517, the guide member 300*b* by the shift and the shear force.

In the second state, the rotary-side insertion portion 537*b* is more shifted relative to the fixed-side insertion portion 517*b* around the central axis of the body portion 31 than in the first state shown in FIG. 11C. The second state shows that the part 537*b*1 on the edge portion of the rotary-side insertion portion 537*b* and the part 517*b*1 on the edge portion of the fixed-side insertion portion 517*b* apply the shear force to the guide member 300*b*, and the part 537*b*1 and the part 517*b*1 press the outer circumferential surface of the guide member 300*b* in the communication part between the rotary-side insertion portion 537*b* and the fixed-side insertion portion 517*b*. The second state shows that the part 537*b*1 and the part 517*b*1 fix the guide member 300*b* by the pressing.

In this case, in the axial direction of the body portion 31, the rotary-side insertion portion 535*b* communicates with the fixed-side insertion portion 515*b*, and the rotary-side insertion portion 535*b* communicates with the rotary-side insertion portion 537*b*.

[Sizes of Fixed-Side Insertion Portions 511 and Rotary-Side Insertion Portion 531]

For the above to be implemented, the lengths of the widths of the fixed-side insertion portion 515*a*, the rotary-side insertion portion 535*a*, the rotary-side insertion portion 537*a*, and the fixed-side insertion portion 517*a* are defined as below.

Fixed-side insertion portion 517*a*≥rotary-side insertion portion 537*a*>rotary-side insertion portion 535*a*≥fixed-side insertion portion 515*a*

For the above to be implemented, the lengths of the widths of the fixed-side insertion portion 515*b*, the rotary-side insertion portion 535b, the rotary-side insertion portion 537b, and the fixed-side insertion portion 517b are defined as below.

Rotary-side insertion portion 535b>fixed-side insertion portion 515b>rotary-side insertion portion 537b≥fixed-side insertion portion 517b

[Advantageous Effects]

Thus, the present embodiment is also applicable to more than one guide member 300. In particular, according to the present embodiment, it is possible to prevent the displacement of each of the guide members 300 or all the guide members 300. According to the present embodiment, even if more than one guide member 300 is used, the proximal end portion 301 of the guide member 300 is inserted through the rotary-side insertion portion 531 and the fixed-side insertion portions 511 in the first state, thereby the holding mechanism 500 holds the proximal end portion 301 of the guide member 300. The rotary holding portion 530 rotates so that the state is switched from the first state to the second state, and the holding mechanism 500 fixes the proximal end portion 301 of the guide member 300. Thus, according to the present embodiment, it is possible to simplify the work of holding and fixing the guide member 300.

Third Embodiment

Figure 12:
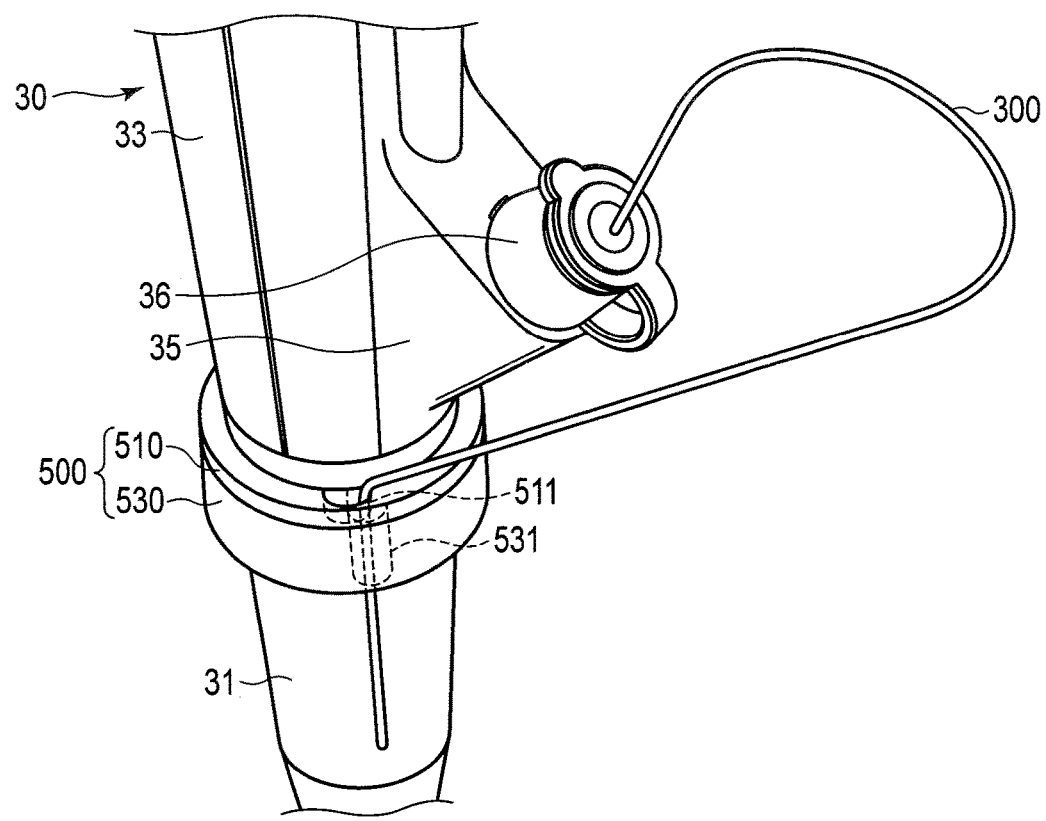
FIG. 12 is a schematic diagram of a holding mechanism according to a third embodiment.

Below, only the differences between the first and second embodiments and the third embodiment are described, with reference to FIG. 12.

Although more than one fixed holding portion 510 and more than one rotary holding portion 530 are provided in the embodiments described above, this is not limitative, as long as one of the first state and the second state is switched to the other. As shown in FIG. 12, one fixed holding portion 510 and one rotary holding portion 530 may be provided if one of the first state and the second state is switched to the other. In this case, the fixed holding portion 510 may be provided on the side of the insertion portion 20, or the rotary holding portion 530 may be provided on the side of the insertion portion 20. Thus, the positional relation between the fixed holding portions 510 and the rotary holding portion 530 does not need to be particularly limited.

The present invention is not completely limited to the embodiments described above, and modifications of components can be made at the stage of carrying out the invention without departing from the spirit thereof. Various inventions can be made by properly combining the components disclosed in the embodiments disclosed above.

What is claimed is:

1. An endoscope comprising:
an insertion portion;
an operation portion coupled to a proximal end portion side of the insertion portion; and
a holding mechanism for one or more endoscope guide members, the one or more endoscope guide members guiding a treatment instrument into a lumen via the insertion portion, wherein
the holding mechanism comprises:
one or more fixed holding portions enclosing at least a part of a circumference of an outer circumferential surface of the operation portion, the one or more fixed holding portions holding a part of a proximal end side of the one or more endoscope guide members exposed from the endoscope at the operation portion; and
one or more rotary holding portions enclosing at least a part of a circumference of an outer circumferential surface of the operation portion;
wherein the one or more rotary holding portions switch a holding state of the one or more endoscope guide members by rotation of the one or more rotary holding portions between:
a first state in which the one or more rotary holding portions, together with the one or more fixed holding portions, hold the part of the proximal end side of the one or more endoscope guide members exposed from the endoscope at the operation portion so that the part of the proximal end side of the one or more endoscope guide members can move relative to the one or more rotary holding portions, and
a second state in which the one or more rotary holding portions, together with the one or more fixed holding portions, fix the part of the proximal end side of the one or more endoscope guide members exposed from the endoscope to prevent the part of the proximal end side of the one or more endoscope guide members from moving relative to the one or more rotary holding portions;
wherein the one or more fixed holding portions comprise a fixed-side insertion portion through which one or more endoscope guide members are inserted and which hold the one or more endoscope guide members by the insertion, and
the one or more rotary holding portions comprise a rotary-side insertion portion through which the one or more endoscope guide members are inserted and which hold the one or more endoscope guide members by the insertion, and
wherein, in the second state,
the rotary-side insertion portion is shifted relative to the fixed-side insertion portion around a central axis of the operation portion more than in the first state, and
in a communication part between the rotary-side insertion portion and the fixed-side insertion portion, a part on an edge portion of the rotary-side insertion portion and a part on an edge portion of the fixed-side insertion portion press an outer circumferential surface of the one or more endoscope guide members while sandwiching the one or more endoscope guide members, whereby the part on the edge portion of the rotary-side insertion portion and the part on the edge portion of the fixed-side insertion portion fix the movement of the one or more endoscope guide members along an axial direction of the one or more endoscope guide members.

2. The endoscope according to claim 1, wherein in the first state, the rotary-side insertion portion communicates with the fixed-side insertion portion, and is provided in alignment with the fixed-side insertion portion, so that the one or more endoscope guide members are movable in the rotary-side insertion portion and the fixed-side insertion portion along the axial direction of the one or more endoscope guide members.

3. The endoscope according to claim 1, wherein the one or more fixed holding portions comprise a pair of fixed holding portions, wherein one of the pair of fixed holding portions and an other of the pair of fixed holding portions sandwich the one or more rotary holding portions in a central axis direction of the operation portion.

4. The endoscope according to claim 3, wherein the one or more endoscope guide members comprise two or more endoscope guide members, two of the two or more endoscope guide members being fixed at two different places at one end portion of the rotary-side insertion portion and the fixed-side insertion portion in one of the pair of fixed holding portions, and at the other end portion of the rotary-side insertion portion and the fixed-side insertion portion in the other of the pair of fixed holding portions, and in the second state, the rotary-side insertion portion is more shifted relative to the fixed-side insertion portion around the central axis of the operation portion than in the first state at the two different places and at the same time.

5. The endoscope according to claim 1, further comprising a positioning mechanism which positions a rotational position of the rotary holding portion in either the first state or the second state.

6. The endoscope according to claim 5, wherein the positioning mechanism comprises a fixed-side positioning portion which is provided in a part fixed to the one or more rotary holding portions that rotate, and a rotary-side positioning portion which is provided in the one or more rotary holding portions and which freely engages with the fixed-side positioning portion, and the fixed-side positioning portion is provided at positions corresponding to the first state and the second state.

7. The endoscope according to claim 6, wherein one of the fixed-side positioning portion and the rotary-side positioning portion comprises a projection portion, and the other comprises a depression portion which detachably engages with the projection portion, and when the one or more rotary holding portions rotate around the central axis of the operation portion, the rotary-side positioning portion engages with one of the fixed-side positioning portions, thereby the one or more rotary holding portions are positioned in the first state, and the rotary-side positioning portion engages with the other of the fixed-side positioning portions, thereby the one or more rotary holding portions are positioned in the second state.

8. The endoscope according to claim 1, wherein the one or more rotary holding portions comprise two or more rotary holding portions and the one or more endoscope guide members comprise two or more endoscope guide members, the two or more rotary holding portions being provided in a same number as the two or more endoscope guide members, the two or more rotary holding portions are provided adjacent to each other along a central axis direction of the operation portion, and the two or more rotary holding portions rotate so that the holding state of the holding mechanism which holds the two or more endoscope guide members switches to either the first state or the second state for each of the two or more endoscope guide members.

9. The endoscope according to claim 1, wherein at least one of the one or more fixed holding portions and the at least one of the one or more rotary holding portions are detachably fixed to the operation portion.

10. The endoscope according to claim 1, wherein the endoscope is a side-viewing endoscope.

11. The endoscope according to claim 1, wherein the one or more endoscope guide members are inserted into the lumen and movable in an axial direction of the insertion portion relative to an opening portion provided in the insertion portion, thereby guiding a treatment instrument, the part of a proximal end side of the one or more endoscope guide members being held by the holding mechanism.

* * * * *